US009028890B2

(12) United States Patent
Ferrari et al.

(10) Patent No.: US 9,028,890 B2
(45) Date of Patent: May 12, 2015

(54) COMPOSITION FOR IMPROVING SEXUAL WELLNESS

(75) Inventors: Victor Ferrari, Cointrin (CH); Frank Schönlau, Münster (DE); Carolina Burki, Cointrin (CH)

(73) Assignee: Horphag Research (IP) Pre Ltd., Limassol (CY)

( * ) Notice: Subject to any disclaimer, the term of this patent is extended or adjusted under 35 U.S.C. 154(b) by 28 days.

(21) Appl. No.: 13/806,876

(22) PCT Filed: Jun. 24, 2011

(86) PCT No.: PCT/IB2011/052788
§ 371 (c)(1),
(2), (4) Date: Mar. 8, 2013

(87) PCT Pub. No.: WO2011/161655
PCT Pub. Date: Dec. 29, 2011

(65) Prior Publication Data
US 2013/0164394 A1 Jun. 27, 2013

Related U.S. Application Data

(60) Provisional application No. 61/344,301, filed on Jun. 25, 2010.

(30) Foreign Application Priority Data

Mar. 21, 2011 (CH) ..................................... 00470/11

(51) Int. Cl.
*A61K 36/00* (2006.01)
*A61K 36/738* (2006.01)
*A61K 31/352* (2006.01)
*A61K 31/198* (2006.01)
*A61K 31/353* (2006.01)
*A61K 36/49* (2006.01)

(52) U.S. Cl.
CPC ............. *A61K 36/738* (2013.01); *A61K 31/352* (2013.01); *A61K 31/198* (2013.01); *A61K 31/353* (2013.01); *A61K 36/49* (2013.01)

(58) Field of Classification Search
None
See application file for complete search history.

(56) References Cited

U.S. PATENT DOCUMENTS

| | | | |
|---|---|---|---|
| 3,436,407 A | 4/1969 | Masquelier | |
| 5,720,956 A | 2/1998 | Rohdewald | |
| 5,904,924 A | 5/1999 | Gaynor et al. | |
| 6,372,266 B1 | 4/2002 | Suzuki et al. | |
| 7,084,122 B2 * | 8/2006 | Larsen et al. | 514/25 |
| 2002/0037862 A1 | 3/2002 | Rohdewald et al. | |
| 2003/0104077 A1 | 6/2003 | Rohdewald et al. | |
| 2004/0137081 A1 * | 7/2004 | Rohdewald et al. | 424/718 |
| 2008/0305096 A1 | 12/2008 | Verdegem et al. | |

FOREIGN PATENT DOCUMENTS

| | | |
|---|---|---|
| CN | 101589802 A | 12/2009 |
| JP | 2004067590 A * | 3/2004 |
| JP | 2004-269487 A | 9/2004 |
| RU | 2388811 C2 | 5/2010 |
| WO | WO 01/91589 A1 | 12/2001 |
| WO | WO 02/14464 A2 | 2/2002 |
| WO | WO 03/043613 A2 | 5/2003 |
| WO | WO 2004/062680 A1 | 7/2004 |
| WO | WO 2008/003314 A1 | 1/2008 |
| WO | WO 2008/115583 A1 | 9/2008 |
| WO | WO 2009/053932 A1 | 4/2009 |

OTHER PUBLICATIONS

Zlatanov, Lipid composition of Bulgarian chokeberry, black currant and rose hip seed oils. Journal of the science of food and agriculture (1999), vol. 79, No. 12, pp. 1620-1624.*
Illes et al, Extraction of hiprose fruit by supercritical CO2 and Propane. Journal of Supercritical Fluids (1997), 10(3), 209-218.*
International Search Report (PCT/ISA/210) & Written Opinion of International Searching Authority for International Application No. PCT/IB2011/052788 mailed on Oct. 26, 2011.
R. Stanislavov, et al., "Improvement of seminal parameters with Prelox: A randomized, double-blind, placebo-controlled, cross-over trial," *Phytotherapy Research*, vol. 2 3, No. 3, pp. 297-302 (Mar. 2009).

* cited by examiner

*Primary Examiner* — Qiuwen Mi
(74) *Attorney, Agent, or Firm* — Harness, Dickey & Pierce, P.L.C.

(57) ABSTRACT

The invention relates to improving sexual fitness or wellness of both sexes, the male sexual enhancement, the treatment of sexual dysfunction and the health of the sexual vascular system of both sexes with ingredients that consist in a source of proanthocyanidins, a source of arginine, rose hip extracts and/or *Quercus robur* extracts. The source of proanthocyanidins may be a botanical extract and the source of arginine may be from arginine aspartate.

14 Claims, 9 Drawing Sheets

Fig. 5.

COMPOSITION FOR IMPROVING SEXUAL WELLNESS

FIELD OF THE INVENTION

The invention relates to improving sexual fitness or wellness of both sexes, the male sexual enhancement, the treatment of sexual dysfunction and the health of the sexual vascular system of both sexes with ingredients that include a source of proanthocyanidins, a source of arginine, rose hip extracts and/or *Quercus robur* extracts. The source of proanthocyanidins may be a botanical extract and the source of arginine may be from arginine aspartate.

BACKGROUND OF THE INVENTION

When a male is in his early twenties, it's easy to take peak sexual performance for granted. Yet as time passes, the male body's biological system changes, and he may notice that his sexual stamina, performance and even pleasure begin to decrease. Getting "in the mood" may start to take a little effort.

Many women have problems with sex when they reach menopause and their ovaries produce smaller amounts of sex hormones. Lower levels of estrogen can make the vaginal tissue dry, and less androgen leads to less sexual desire and arousal.

One important difference affecting sexual desire is that men have levels of testosterone that are 20 to 30 times what women have. Men's testosterone levels gradually decline over time but they do not experience a drop-off as women do at menopause. In men and women, testosterone and other androgens work to increase desire.

Androgen gels and patches for women are being considered for women with sexual dysfunction. Another possibility to overcome the female androgen deficiency syndrome is to supply women with 50 mg dehydroepiandrosterone per day, which facilitates the enhanced production of testosterone, dehydrotestosterone, androstenedione and androstenediol. That improved female androgenic profile causes intense sexual thoughts and a general enhancement in mental and physical sexual arousal (Spark, R. F., 2002; Hackbert, L. and Heiman J. R., 2002).

To increase blood flow in the female genital tissue is also useful to improve sexual wellness. The New York Times on Mar. 25, 2003 published an article entitled "Effort to Make Sex Drug for Women Challenges Experts". According to the article, researchers found that women's sex organs are not as readily affected as men's by sildenafil, which is the active ingredient of a drug sold under the trademark VIAGRA®. Blocking the same enzyme in women that normally inhibits blood flow does not increase circulation to genital tissue so drastically as in men for causing engorgement of erectile tissue. Studies suggest that sildenafil alone does not fix female arousal problems. However, when taken together with supplemental hormones, at least one study showed that 57 percent of 202 postmenopausal women involved in a study reported improved genital sensations, compared with 43 percent of a placebo group. Forty-one percent of the sildenafil group members reported greater satisfaction with sex, compared with 27 percent in the placebo group. Although the differences between the two groups were modest, the study suggests that sildenafil could help women with healthy hormone levels and in happy relationships. Nevertheless sildenafil is a medicament that needs a strict prescription since the side effects are numerous.

One may surmise that female sexual function is accomplished physiologically in a similar manner like in man in a way that cGMP triggers lubrication and engorgement of the clitoral tissue. The studies mentioned in the previously mentioned article suggest the possibility that when women have a healthy hormone level, such dietary supplements may help improve sexual function in women to some extent. Another way to increase the blood flow into the female or male sexual organs is to increase the production of nitric oxide, which in turn triggers the release of cGMP. Whereas sildenafil and related substances lead to a sustained increase of blood content of the male or female sexual organs by blocking the enzymatic destruction of the vasodilating cGMP, nitric oxide produces the same increased blood volume by enhancing the production of cGMP. As a physiological source for nitric oxide production, the aminoacid L-arginine is used.

The enzyme endothelial nitric oxide synthase produces nitric oxide from L-arginine. To provide an enhanced and sustained blood flow to the sexual organs, it is first of all necessary to supplement the organism with the substrate L-arginine in sufficient quantities. However, the presence of high concentrations of L-arginine alone does not lead to a substantial higher blood flow to the sexual organs. It is necessary to stimulate additionally the endothelial nitric oxide synthase, so that nitric oxide production from L-arginine is catalyzed by the active enzyme. A potent stimulator of endothelial nitric oxide synthase is a proanthocyanidins-containing extract.

Proanthocyanidins represent a group of plant polyphenols found in roots, barks and fruits with an astringent taste. Proanthocyanidins include the subgroups of procyanidins and prodelphinidins. Proanthocyanidins are biopolymers composed of flavan subunits. Procyanidins are composed of catechin and epicatechin units, also called monomeric procyanidins.

Proanthocyanidins are extracted from plant material by conventional methods using solvents like water, ethanol or acetone or fluid carbon dioxide. The extracts are purified by solvent/solvent extraction, ultra filtration or chromatographic procedures. The purified extracts are concentrated by solvent evaporation, freeze drying or spray drying.

A proanthocyanidin-rich extract from the bark of French maritime pine is distributed under the tradename Pycnogenol® by Horphag Research, Switzerland. The extract contains 70-75% by weight procyanidins and other flavanols such as catechin, epicatechin and taxifolin. Other proanthocyanidins rich extracts can be obtained from grape seeds, cones from cypress trees, cocoa beans or other plant materials. Pycnogenol® pine bark extract has been shown to stimulate endothelial nitric oxide synthase and to induce vasodilation (Fitzpatrick, D. F., Bing, B., Rohdewald, P., 1998).

US 2004137081 A1 (Rohdewald P. et al.) discloses that sexual wellness or sexual fitness is enhanced over time by administrating on a daily basis a source of proanthocyanidins and a source of arginine. Both sources may be blended into a composition or taken separately from a kit. The source of arginine may be a salt or peptide of L-arginine and aspartic acid such as arginine aspartate. The proanthocyanidins stimulate an endothelial NO-synthase enzyme, which serves as a catalyst for synthesis of the nitric oxide from a substration that is the source of the arginine. A sufficient amount of the nitric oxide is released over time to enhance sexual wellness or sexual fitness. In case of low levels of androgenic hormones in both sexes, the combination may contain as a further ingredient a sex hormone or a sex hormone precursor or a sex hormone stimulant or a sex hormone bioavailability enhancer.

WO 2008/115583 A1 (Mini John) uses the principles of traditional Chinese medicine in systematic and non-traditional ways to arrive at balanced formulas that bring about the goals desired in Chinese Medicine without hindering the digestibility of the formulations or taxing the user's organs. For example, the disclosed formulations utilize a number of adaptogenic herbs, traditional medicinal herbs and highly nutritious food substances, which allow the body to assimilate these substances and bring them to where they can best be used to treat the conditions or reduce various the side effects disclosed.

WO 01/91589 A1 (SIGMA TAU HEALTHSCIENCE SPA) discloses a health food/dietary supplement with antioxidant activity, comprising as its characterising components an alkanoyl carnitine and a combination of polyphenols extracted from trees or shrubs.

US 2008305096 A1 (UNICITY INTERNATIONAL INC) discloses a method of providing controlled release of a biologically active substance within a subject's digestive system. The biologically active substance is administered concurrently with one or more soluble fibers in an oral dosage unit. The soluble fibers interact with the biologically active substance within the subject's digestive system to moderate and control the release of the biologically active substances in the subject's bloodstream. This provides more constant blood concentrations of the biologically active substances. The amount of soluble fibers in the oral dosage unit is greater than 40% by weight, and in some cases greater than 50% by weight of the oral dosage unit. The oral dosage unit typically contains from about 1 to 15 g of soluble fiber, and in some cases from about 3 to 5 g of soluble fiber. The biologically active substance may contain phytonutrients that promote the subject's cardiovascular system, immune system, or weight management.

JP 2004269487 A (Efuekuto K K et al.) provides a method in which a high purity proanthocyanidin can be produced by a simple means. This method for producing proanthocyanidin is characterized by extracting it from peanut seeds as it is with water, a water-miscible organic solvent or a mixture thereof. Further this document relates to proanthocyanidin obtained by the method, that having specified physicochemical properties, an extract from peanut seeds having specified physicochemical properties, and a medicinal composition, cosmetic or foodstuffs containing proanthocyanidin or the extract from peanut seeds.

RU 2388811 C2 (OOO TJUMEN) discloses a composition of components for production of medicinal balsam containing, per 1000 dhal of balsam, water pepper (root part)—5 kg. Liquorice (root)—5 kg. Heliotrope (root)—0.5 kg. Common origanum—3 kg. Cloves—3 kg. Cinnamon—2 kg. John's-wort—6 kg. Common cherry (kernel powder)—5 kg. Coriander—3 kg. Corn snouts—0.5 kg. Peppermint—3 kg. Oak sawdust—2 kg. Plantain—2 kg. Artemisia austriaca—3 kg. Hungarian sainfoin (roots and stems)—5 kg. Yarrow—2 kg. Sage—3 kg. Thyme—3 kg. Sorrel—1 kg. Chicory—3 kg. Field eryngo (roots and stems)—5 kg. White cornelian cherry—28 kg. Haw—14 kg. Rosehips—21 kg. Alcoholised cherry plum juice—1000 kg. Alcoholised apple juice—1500 kg. Sugar for syrup—870 kg. Sugar for dye—560 kg. Vanillin—1 kg. Rose tincture—1 l.; Rectified ethyl alcohol in the amount required for a 43% proof and softened water—balance. The balsam alcohol proof (vol) is 43%, total extract is 16.8 g/100 cm3, the balsam has a specific taste, colour and aroma. The composition is used for the improvement of the balsam medicinal properties as a remedy against sexual weakness of men and women that enhances vigour and vitality.

Sexual dysfunction (SD), particularly in postmenopausal, healthy (>55) women, is currently insufficiently understood, partially because of the great difficulty most women have to openly discuss these problems. Sexual dysfunction is suggested to be more common in women (43%) than in men (31%). The incidence and perception of sexual dysfunction are very different considering population type, age, social class, income, education and women's priorities.

The incidence of SD in women increases with age and with the presence of chronic diseases (i.e., diabetes).

Treatment with drugs, such as those used for hypertension and hyperlipidemia, may have negative effects on sexual function and interest. Vaginal dryness is progressively more frequent with age, and vaginal infections are more common with increasing age and in diabetic women. They may cause SD, loss of interest, and difficult or painful intercourse that can be associated with anxiety and fear, contributing to a lack of motivation. In diabetic women, microangiopathy, neuropathy and edema, in association with frequent subclinical or clinical infections, cause mucosal alterations, altered responses to sexual stimulations, and eventually chronic vaginal dryness, which may become a key element in altering sexual life and may lead to sexual dysfunction.

However, these problems may also occur in apparently healthy women. Recent studies have evaluated these problems and possible solutions. The Female Sexual Function Index (FSFI) has been established and utilized in several studies to assess sexual function.

There is still a need for an effective and safe composition for improving sexual fitness or wellness of both sexes, the man sexual enhancement, the treatment of sexual dysfunction.

SUMMARY OF THE INVENTION

One aspect of the invention resides in a product that, when administered, offers both sexes a safe, natural way to preserve and maintain sexual responsiveness, endurance and enjoyment. It includes a blend or preparation of ingredients, namely, a source of proanthocyanidines, a substrate that is a source of arginine, preferably a salt or dipeptide of L-arginine and aspartic acid, such as arginine aspartate or citrulline or ornithine or any arginine precursors or derivatives, rose hip extracts and/or *Quercus robur* extracts or a mixture thereof. When the blend is administered, the endothelial NO-synthase is stimulated by the proanthocyanidins. Nitric oxide is released from the substrate in response to the stimulated endothelial NO-synthase enzyme, which acts as a catalyst for synthesis of the nitric oxide from the substrate. The source of arginine and proanthocyanidins are in therapeutically effective amounts to cause a sufficient amount of the nitric oxide to be released from the synthesis so that when fresh supplies are taken on a daily basis over a period of time, sexual fitness or sexual wellness improves by the end of the period of time.

In one aspect of the present invention there is provided a preparation consisting in the combination of a source of arginine and a source of proanthocyanidins as well as Rose hip and/or extracts thereof or *Quercus robur* and/or extracts thereof or a mixture of Rose hip and *Quercus robur*.

In another aspect, the present invention provides for a dietary or food supplement, a food preparation, a beverage, a medicament and a topical preparation comprising the preparation of the present invention.

In a further aspect, the preparation of the present invention is provided for improving sexual fitness or wellness of both sexes, the man sexual enhancement, the treatment of sexual dysfunction and the health of the sexual vascular system of both sexes.

BRIEF DESCRIPTION OF THE FIGURES

FIG. 5. Illustrates a comparative analysis of WHQ symptoms for each visit by group.

DETAILED DESCRIPTION OF THE INVENTION

Figure 1:
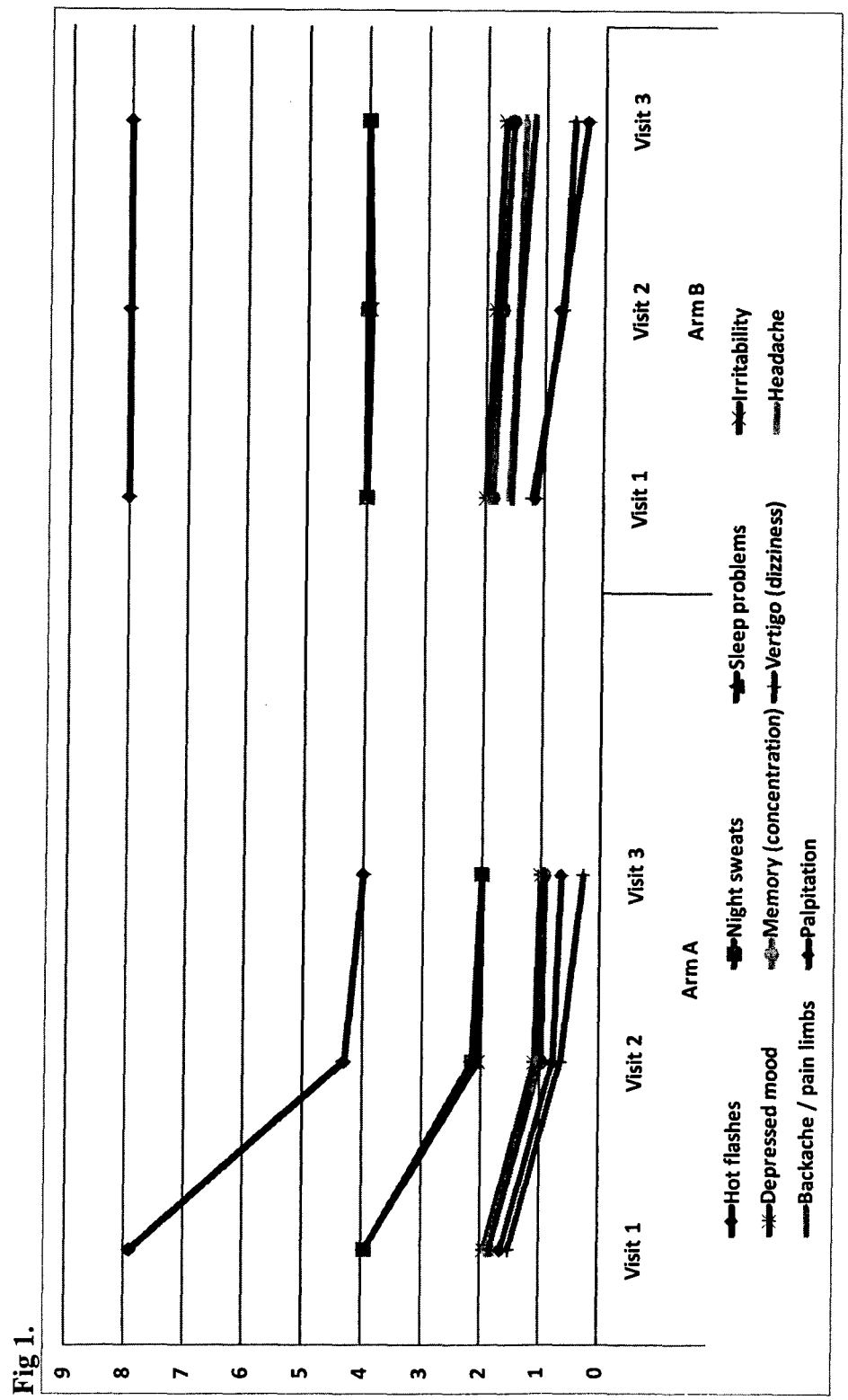
FIG. 1. Shows a comparative analysis of Kupperman's index by visit for arm A and arm B: Arm B.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

As used herein the term "pine bark extract" refers to a French maritime pine bark extract which is, for example, commercially available as Pycnogenol® (Horphag). The terms "Pycnogenol®", "pine bark extract" and "French maritime pine bark extract" are interchangeable. *Pinus pinaster* (*P. pinaster*) and *Pinus maritima* (*P. maritime*), are understood to refer to the same organism commonly called "French Maritime Pine." Hence, these terms are interchangeable.

The term "extract", as used herein includes any preparation obtained from plants, fruits, roots or vegetables using an extraction method.

The term "food preparation" refers generally to material of either plant or animal origin, or of synthetic sources, that contain essential nutrients such as a carbohydrate, protein, fat, vitamin, mineral, etc. used in the body of an organism to sustain growth, repair, and vital processes and to furnish energy.

A "dietary or food supplement" refers to a product that contains substances like vitamins, minerals, foods, botanicals, amino acids and is intended to supplement the usual intake of these substances. Dietary supplements are found in pill, tablet, capsule, powder or liquid form and are meant to be taken by mouth.

The term "nutraceutical" refers to any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It also refers to a product isolated or purified from foods, and generally sold in medicinal forms not usually associated with food and demonstrated to have a physiological benefit or provide protection against diseases like chronic diseases for example.

The term "beverage" means a liquid for drinking, which may be water, flavored water, soft drinks, alcoholic drink, health drink, or an enriched drink like based on a diary product (milk) or fruit juice.

"Pharmaceutically acceptable excipients or carriers" are any materials that do not interfere with the pharmacological activity of the active ingredient(s) or degrade the body functions of the subject to which it can be administered but facilitate fabrication of dosage forms or administration of the composition. Examples of pharmaceutically acceptable excipient include but are not limited to maltodextrin, calcium phosphate, and fused silica. Pharmaceutically acceptable excipients also include flavorants, as well as various additives such as other vitamins and minerals, all solvents, dispersion media, coatings, isotonic and absorption delaying agents, sweeteners and the like, non-toxic auxiliary substances such as wetting or emulsifying agents, pH buffering agents and the like, such as for example, sodium acetate, sorbitan monolaurate, triethanolamine oleate, and inert ingredients such as talc and magnesium stearate which are standard excipients in the manufacture of tablets, capsules and other dosage forms.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

"Fitness", whether "sexual fitness" or physical fitness, is defined as a measure of efficient functioning. A person who is sexually fit is efficient in their capacity to think, feel, and behave in a sexual manner without shame, embarrassment, or hidden agendas of falsely boosting their ego or self-esteem. People who reach and practice this style of fitness are more likely to function efficiently in all aspects of their perceptual world. These fortunate individuals are more confident, physically ill less often, and manage stressful events more successfully. Sexual fitness is an achieved state of being allowing people to perform better in every action they engage in. Having this capability affords person to feel confident in all situations whether a partner is involved or not.

"Sexual wellness" of both sexes is the active participation of the individual in his or her life by addressing the numerous issues within sexual health. The process defined as sexual wellness is to improved sexual health. "Sexual health" is a state of physical, mental and social well-being in relation to sexuality. It requires a positive and respectful approach to sexuality and sexual relationships, as well as the possibility of having pleasurable and safe sexual experiences, free of coercion, discrimination and violence (definition WHO 2002). In particular, Sexual health is the integration of the somatic, emotional, intellectual, and social aspects of sexual being, in ways that are positively enriching and that enhance personality, communication, and love. Fundamental to this concept are the right to sexual information and the right to pleasure (definition of WHO 1975). Sexual health is inextricably bound to both physical and mental health.

"Male sexual enhancement" may be defined as the increase of the hardness of erection; the improvement of self-confidence; the improvement of sperm quality, count and motility (spontaneous motion) and fertility; the increase of libido and sex drive; the boosting of the sexual energy level and vitality; the improvement of sexual performance problems i.e. those due to aging as well as the increase of energy and the greater sexual satisfaction with a partner. Men's sexual function is scored using the established "International Index of Erectile Function" (IIEF) questionnaire [Rosen et al., 1997], see i.e. example 4. www.seekwellness.com/mensexuality/questionnaire.htm "Female sexual enhancement" is defined as anything that enhances a woman's sexuality; this includes in particular the increase of libido or sex drive. Low libido or sex drive in women can be caused by a number of factors that vary from one woman to another; fatigue, mild depression, and the multiple roles that women play in daily life can cause psychological issues, which can have an affect on a woman's sexual appetite. Antidepressants, birth control, tranquilizers and mood stabilizers also impact sexual activity and other conditions like diabetes, heart disease and a poor diet can also reduce a woman's sex drive. Woman's sexuality level may be determined by the Female Sexual Function Index (FSFI) and the Women's Health Questionnaire (WHQ) which are defined and detailed in example 2.

"Sexual dysfunction" or sexual malfunction in both sexes refers to a difficulty experienced by an individual or a couple during any stage of a normal sexual activity, including desire, arousal or orgasm. Sexual desire disorders or decreased libido are characterized by a lack or absence for some period of time of sexual desire or libido for sexual activity or of sexual fantasies. Sexual arousal disorders were previously known as frigidity in women and impotence in men, though these have now been replaced with less judgmental terms. Impotence is now known as erectile dysfunction, and frigidity has been replaced with a number of terms describing specific problems with, for example, desire or arousal. For both men and women, these conditions can manifest themselves as an aversion to, and avoidance of, sexual contact with a partner. In men, there may be partial or complete failure to attain or maintain an erection, or a lack of sexual excitement and pleasure in sexual activity.

Erectile dysfunction or impotence is a sexual dysfunction characterized by the inability to develop or maintain an erection of the penis. The causes of erectile dysfunction may be psychological or physical.

Orgasm disorders are persistent delays or absence of orgasm following a normal sexual excitement phase. The disorder can have physical, psychological, or pharmacological origins.

Sexual pain disorders affect women almost exclusively and are known as dyspareunia (painful intercourse) or vaginismus (an involuntary spasm of the muscles of the vaginal wall that interferes with intercourse).

Proanthocyanidins designates a group of flavonoids that includes the subgroups procyanidins, prodelphinidins and propelargonidins. Proanthocyanidins are homogeneous or heterogeneous polymers consisting of the monomer units catechin or epicatechin, which are connected either by 4-8 or 4-6 linkages, to the effect that a great number of isomer proanthocyanidins exist. Typically, the proanthocyanidins oligomers have a chain length of 2-12 monomer units. Proanthocyanidins may be synthesized or extracted from a plant material. Non-limiting examples of plant material sources of proanthocyanidins include grape seeds, grape skin, pine barks, ginkgo leaves, peanuts, cocoa beans, tamarind, raspberries, currants (black), peanut, almond, apple, cranberry, blueberry, tea leaves. Preferably the source of proanthocyanidin consisting of a plant extract is selected among a pine bark extract, a grape seed extract or an extract of apples, peanut skin, walnuts, pomegranates, raspberries, currants (black), blueberries, almonds, tea, hawthorn or cocoa or combination thereof. Those plant extracts are also referred as "proanthocyanidin rich extracts".

A well-known product containing proanthocyanidins, which is available in trade as a preparation of a food supplement under the name Pycnogenol®, is an extract of the French maritime pine bark (*Pinus pinaster*), see also U.S. Pat. No. 3,436,407 (MASQUELIER JACQUES); U.S. Pat. No. 5,720,956 (ROHDEWALD, PETER) and U.S. Pat. No. 6,372,266 (SUZUKI NOBUTAKA et al. Horphag Research Ltd.) which are incorporated herein by reference. Pycnogenol® is a standardized bark extract of the French maritime pine *Pinus pinaster*, Aiton, subspecies Atlantica des Villar. The quality of this extract is specified in the United States Pharmacopeia (USP 28) (Maritime Pine Extract. In: United States Pharmacopeia. Rockville: United States Pharmacopeial Convention, Inc.; 2005. pp. 2115-2116). The extract consists of a concentrate of polyphenols, which are also contained in fruits and vegetables, but, in low concentrations. The polyphenols are composed from flavonoids, especially procyanidins, and phenolic acids. All these constituents possess the ability to inactivate free radicals. Rohdewald P. A review of the French maritime pine bark extract (Pycnogenol®), a herbal medication with a diverse pharmacology. Int J Clin Pharmacol Ther 2002; 40(4): 158-168. Between 65-75% of Pycnogenol® in weight are procyanidins comprising of catechin and epicatechin subunits with varying chain lengths (Rohdewald P. A review of the French maritime pine bark extract (Pycnogenol®), an herbal medication with a diverse clinical pharmacology. Int J Clin Pharmacol Ther 2002; 40: 158-168). Other constituents are polyphenolic monomers, phenolic or cinnamic acids and their glycosides (Id.).

The composition comprising proanthocyanidins, present in the preparation of the invention, is originated from a plant extract or from a synthesized material (i.e., synthetic proanthocyanidins).

The plant extract can be selected from the group consisting of proanthocyanidins containing extracts selected among extracts of pine bark, the cones of cypresses grape seed, apples, peanut skin, walnuts, pomegranates, tomatoes, almonds, tea, hawthorn, cocoa or combination thereof. Proanthocyanidins containing rich extracts are natural and preferably plant extracts having more than 50% by weight (of dried extracts) of proanthocyanidins, more preferably more than 70% by weight and even more preferably more than 75% by weight of proanthocyanidins. Preferably the plant extract according to the present invention is originated from pine bark and more preferably the plant extract is Pycnogenol®.

In a preferred embodiment, the composition comprising proanthocyanidins may be a pine bark extract. The pine bark may be from *P. pinaster*, such as, for example, from Pycnogenol®. In a preferred embodiment, the composition may contain proanthocyanidins at a concentration of 10% to 100% of total weight. For example, a Pycnogenol® composition may be diluted or concentrated to contain 10%, 20%, 30%, 40%, 50%, 60%, 70%, 75%, 80%, 90% or 95% proanthocyanidins. Concentration may be performed using known methods such as column chromatography or affinity chromatography.

The composition also contains rose hip extract, which is a naturally occurring source for the glycoside of mono- or di- or triacylglycerol compounds. The rose hip is preferably obtained from wild rose bushes, in particular the rose hip is selected from the group consisting of *Rosa canina* ("dog rose hip"), *Rosa gallica, Rosa condita, Rosa rugosa, Rosa hugonis, Rosa nitida, Rosa pendulina, Rosa pimpinellifolia*, and *Rosa sericea*. Preferably, the rose hip extract is in powdered form and may be pelletized or placed in capsules with a physiologically acceptable carrier for formulation into unit dosages. Rose hip extracts comprise carotenoids, tocopherols, tocotrienols, vitamin C, polyphenols as well as glycosides of mono- or di- or triacylglycerol.

The term "glycosides of mono- or di- or triacylglycerol" and similar terms are intended to mean a class of glycosides of mono- or di- or triacylglycerols (as well as ethers), such as those which may be isolated from plants e.g. as illustrated by the methods described in WO 2008/003314 A1 or WO 03/043613 A1, and which are not esters of eicosapentaenoic acid. The "glycoside" part is typically a pentose, hexose or heptose, in particular hexoses such as galactose and glucose, e.g. galactose, but may also be di- and oligosaccharides containing two or more sugar moieties in combination, in particular diglycosides such as digalactosides and diglucosides, e.g. 6-O-([alpha]-D-galactopyranosyl)-[alpha]-D-galactopyranose. The most preferred galactolipid is e.g. 3-[beta]-D-galactopyranosyloxy-2-(octadeca-9Z,12Z,15Z-trienoyloxy) propanyloctadeca-9Z,12Z,15Z-trienoate (GOPO).

In the present context, the term "glycosides of mono- or di- or triacylglycerol product" relates to a product obtained from a plant material comprising a glycoside of mono- or di- or triacylglycerol compound also referred as "Rose hip extracts". The glycosides of mono- or di- or triacylglycerol product may be obtained from the plant material by isolation by means of chromatography, microfiltration, filtration, centrifugation, extraction or any combination thereof.

Glycosides of mono- or di- or triacylglycerol compounds, isolated from plant material such as rose hips. The rose hip is preferably obtained from wild rose bushes, in particular the rose hip is selected from the group consisting of *Rosa canina* ("dog rose hip"), *Rosa gallica, Rosa condita, Rosa rugosa, Rosa hugonis, Rosa nitida, Rosa pendulina, Rosa pimpinellifolia*, and *Rosa sericea*.

The plant material is not limited to rose hip only. It might consist of any plant material containing a glycoside of mono- or di- or triacylglycerol compounds, and especially galactolipids, such as fruit, vegetables or cereals, where the fruit, vegetable or cereal is preferably selected from the group consisting of olive (e.g. *Olea europaea*), alfalfa (e.g. *Mediargo sativa* L.), soya bean (e.g. *Glycine max*), potato (e.g. *Solanum Turerosum* L.), pepper (e.g. *Capsicum annuum* L.), oat (e.g. *Avena sativa*), wall cress (e.g. *Arabidopsis thaliana*), Petunia hybrida, lyme grass (e.g. *Elymus arenarius*), broom (e.g. *Sarothamnus scoparius*), coltsfoot (e.g. *Tussilago farfara*), chenopodiaceae, seakale (e.g. *Crambe maritima*), sloe (e.g. *Prunus spinosa*), eryngo (e.g., *Eryngium*), sea purslane (e.g. *Honckenya peploides*), blackberry, mountain ash (e.g. *Sorbus aucuparia*), service tree (e.g. *Sorbus domestica*), sea buckthorn (e.g. *Hippophae rhamnoides*), hemp agrimony (e.g. *Eupatorium cannabinum*), cucumber (e.g. *M. charantia* or *M. rustrata*), Catharanthus roseus, yew (e.g. *Taxus baccata*), mistletoe (e.g. *Viscum album*), horsetails (e.g. *Equisetum arvense*), meadowsweet (e.g. *Filipendula ulmaria*), dropwort (e.g. *F. hexapetala*), Ephidera (e.g. *E.* sp.), reed (e.g. *Phragmites communis*), ground ivy (e.g. *Glechoma hederacea*), male fern (e.g. *Lastrea filix* mas), shield fern (e.g. *Dryopteris*) and lady's mantle (e.g. *Alchemilla vulgaris*); seaweed, preferably, the seaweed is selected from the group consisting of Anfeltia tobuchiensis (Rhodophyta), Laminaria japonica, Sargassum pallidum (Phaeophyta), Ulva fenestrate (Chlorophyta), Zostera marina (Embriophyta), sea wrack (Fucus vesiculosus), green alga (Chlorella vulgaris), Cyanobacteria (e.g. Phormidium tenue) and Okinawan Marine Sponge (Phyllospongia Foliascens).

"*Quercus robur*" also know as "oak wood" belongs to the family of Fagaceae and the genus *Quercus*. *Quercus robur* (sometimes considered *Q. pedunculata*) is commonly known as Pedunculate oak or English oak. Also included in this definition of "oak wood" is the white oak, *Quercus alba, Quercus brutia Tenore, Q. pedunculiflora, Q. haas* as well as the Sessile Oak (*Q. petraea*). In the present invention the term "*Quercus robur*" will be considered as equivalent to oak wood as defined above, they are interchangeable.

Gathering: felling of the trees under National Forest Office control, from October to April when the sap is down. Oak wood is traditionally used to make wine barrels and is known to give its taste to wine and to contribute to its antioxidant activity. Fresh wood chips used for Biolandes extract are purchased from a famous wine barrel maker (www.dargaud-jaegle.com/) and obtained from Oak trees rigorously selected.

The extraction process is carried out by water extraction at low temperature (50° C.) and spray drying. No petrochemical solvent is used.

Oak wood extract contains ellagitannins (Roburins A, B, C, D, E, Vescalin, Castalin, Vescalagin, Castalagin) and phenolic acids (gallic acid, ellagic acid).

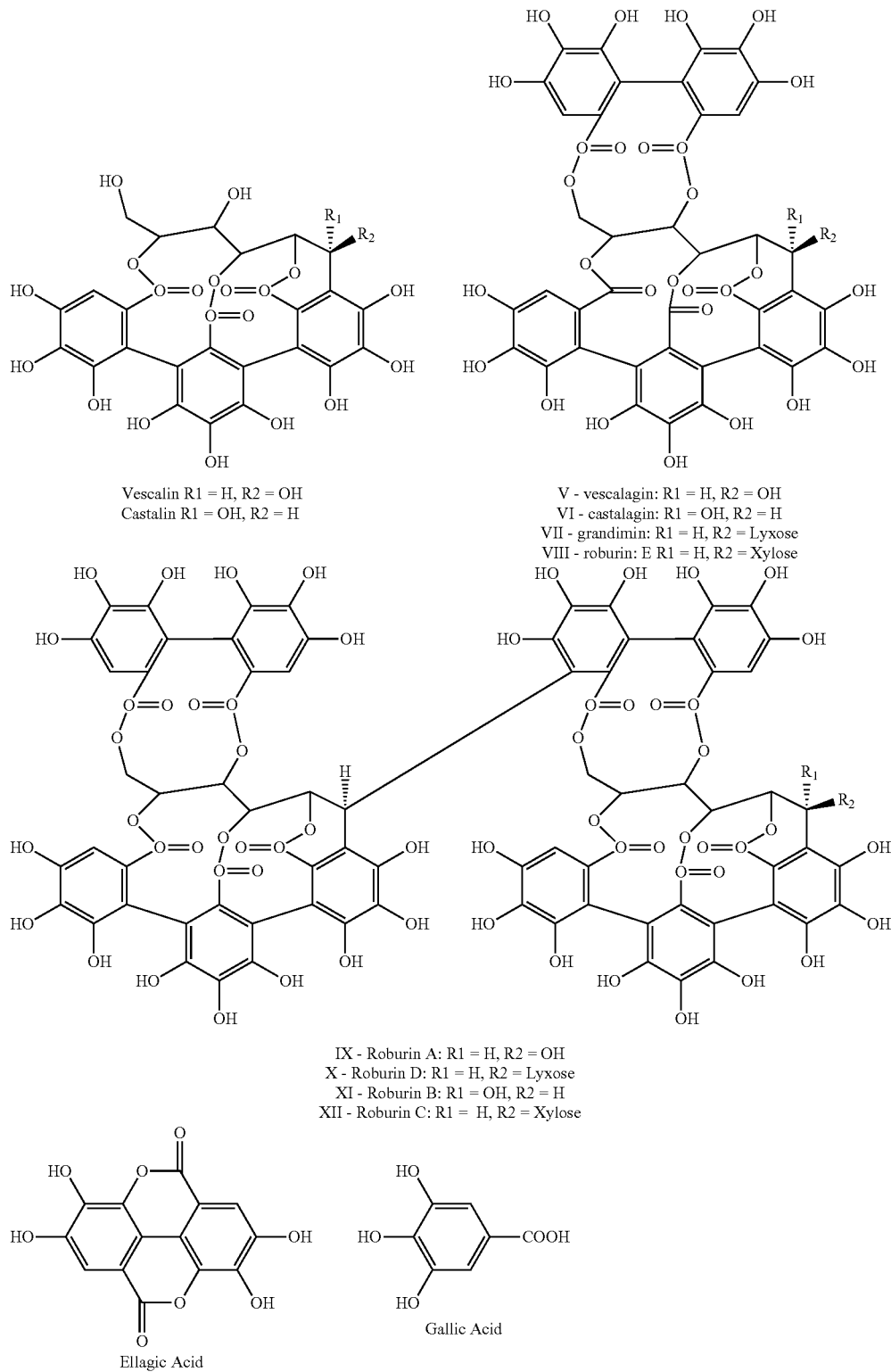

The invention pertains to the prolonged use of a blend of ingredients, namely, a substrate that is a source of arginine, such as arginine aspartate or citrulline or ornithine or any arginine precursors or derivatives, preferably a salt or dipeptide of L-arginine and aspartic acid, a source of proanthocyanidines and Rose hip or extracts thereof or *Quercus robur* or extracts thereof or a mixture of Rose hip or extracts thereof and *Quercus robur* or extracts thereof. Preferably, the source of arginine is a salt or peptide of arginine and aspartic acid, namely, arginine aspartate. Preferably, the source of proanthocyanidins is derived from Pycnogenol® or from other proanthocyanidin-containing extracts.

An oral administration of the blend in accordance with an administration regimen over a prolonged period of time provides certain benefits, which include helping to protect, restore and sustain blood vessel health and improve blood flow to the genital area, naturally enhancing male erections or female tumescence, naturally enhancing the body's sexual response and improving the health of the sexual vascular system.

By orally administering the blend of a source of arginine, the Rose hip or extracts thereof and a source of proanthocyanidins, the benefits to sexual fitness or sexual wellness are realized. That is, over time, the cumulative effect of the blend leaves one experiencing a heightened sense of sexual well-being.

The blend or preparation of the present invention may be in the form of a composition, taken either in tablet form or in liquid form. Alternatively, the blend may be in the form of the ingredients being in separate, distinct tablet or liquid form but packaged together in a kit. In the latter case, the separate ingredients are taken either simultaneously, such as by mixing them together if in liquid form, or one after another if in tablet form.

In particular the present invention concerns a preparation comprising the combination of a composition comprising proanthocyanidins a source of arginine and a composition comprising Rose hip and/or extracts thereof.

Preferably, the preparation comprises the combination of a composition consisting of proanthocyanidins and a composition consisting of Rose hip and/or extracts thereof, and a suitable excipient.

In another embodiment of the invention, the preparation further comprises *Quercus robur* (oak wood) and/or extracts thereof and a suitable excipient q.s.p.

In particular, the preparation of the invention consists in a combination of:
  a source of proanthocyanidins,
  a source of arginine,
  Rose hip and/or extracts thereof or *Quercus robur* and/or extracts thereof or a mixture thereof, and a suitable excipient.

Proanthocyanidins of the invention are originated from a plant extract or from a synthesized material.

Preferably, the plant extracts is selected from the group consisting of proanthocyanidins containing extracts selected among extracts of pine bark, grape seed, apples, peanut skin, walnuts, pomegranates, raspberries, currants (black), blueberries, almonds, tea, hawthorn, cocoa or combination thereof.

More preferably, the plant extract is originated from pine bark and even more preferably this plant extract is originated from the French maritime pine bark (Pycnogenol®).

According to the invention Rose hip and/or extracts comprise carotenoids, tocopherols, tocotrienols, vitamin C, polyphenols and glycosides of mono- or di- or triacylglycerol compounds.

While drugs for sexual enhancement may offer a temporary solution or tempting "quick fix," they are associated with unwanted side effects and can be expensive. The blend according to the present invention, which is a natural dietary supplement, offers a safe, natural and cost-effective alternative.

The suitable excipient of the invention is an acceptable excipient or carrier as defined above.

Examples of suitable excipients of this invention include, but are not limited to, anti-adherents, binders (e.g., macrocrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof.

For example, the preparation of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

Optionally the preparation of the present invention may include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and combinations thereof.

In a preferred embodiment of the invention, the suitable excipient is a pharmaceutically acceptable excipient.

The present invention further provides for a food preparation, a dietary or food supplement, a nutraceutical, a beverage, a medicament and a topical preparation comprising the preparation of the present invention.

Preferably, the dietary supplement, the nutraceutical or the medicament of the present invention is administered at a dosage of between 5 mg per day to 2,000 mg per day. Preferably between 50 mg to 1,000 mg per day and even more preferably between 100 mg to 400 mg per day.

The preparation, the dietary supplement, the nutraceutical or the medicament of the present invention can be administered orally, parenterally or topically at a dosage of between 5 mg per day to 2,000 mg per day. Preferably between 50 mg to 1,000 mg per day and more preferably between 100 mg to 400 mg per day.

If intended for oral administration, the medicament of the present invention can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a solution for intravenous, intramuscular or subcutaneous injection.

The topical preparations according to the present invention can be, but not limited to, a cream, a patch, a gel, an ointment, a lotion, a tincture, a spray, a mousse, a cleansing composition or a foam. The topical preparations of the present invention can be also in the form of a suspension or dispersion in solvents or fatty substances, or alternatively in the form of an emulsion or micro emulsion, PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

Also encompassed by the present invention is a method of improving sexual fitness or wellness of both sexes comprising administering to a subject in need thereof an effective amount of the preparation or the medicament of the invention.

The invention also provides for a method of improving man and female sexual enhancement comprising administering to a subject in need thereof an effective amount of the preparation or the medicament of the invention.

The invention also concerns a method of treating or preventing sexual dysfunction in both sexes comprising administering to a subject in need thereof an effective amount of the preparation or the medicament according to the invention.

The methods according to the invention enhance a level of sexual wellness for both sexes, comprising ingredients that include:
a substrate as a source of arginine and, subsequently, for nitric oxide; and
a stimulator that includes proanthocyanidins in an amount to stimulate an endothelial NO-synthase enzyme, which serves as a catalyst for synthesis of the nitric oxide; Rose hip or extract thereof and/or *Quercus robur* (oak wood) or extracts thereof.

The ingredients being in therapeutically effective amounts so that, when the ingredients are administered at least daily over a period of time, a sufficient amount of the nitric oxide releases from the synthesis to enhance a level of sexual wellness by an end of the period of time.

The methods of the invention also help in attaining enhanced sexual wellness by stimulating nitric oxide synthase enzyme and releasing nitric oxide, comprising: administering the preparation daily over a period of time. The administering includes initially administering an elevated dosage of the preparation to attain the enhanced level of sexual wellness by the end of the period of time and thereafter administering a dosage of the composition daily that contains less of the composition than the elevated dosage and still provide the enhanced level of sexual wellness.

Preferably, the preparation or the medicament is administered orally, parenterally or topically as defined above.

In one embodiment of the invention, the preparation or the medicament of the invention is administered at a dosage of between 5 mg per day to 2,000 mg per day. The subject in need thereof is a mammal, preferably a human.

The medicament or the dietary supplement of the invention is for example adapted for use in improving sexual fitness or wellness of both sexes, for use in improving man sexual enhancement such as sperm production or fertility and/or for use in treating or preventing sexual dysfunction in both sexes.

Another object of the present invention is a composition consisting in the combination of a source of proanthocyanidins, a source of arginine and *Quercus robur* (oak wood) and/or extracts thereof. Preferably the composition may further comprise Rose hip and/or extracts thereof and a suitable excipient q.s.p.

The latter composition is for example adapted for use in improving sexual fitness or wellness of both sexes, for use in improving man and female sexual enhancement and/or for use in treating or preventing sexual dysfunction in both sexes.

A unit dosage comprises a therapeutically effective daily amount of the preparation (a source of proanthocyanidins, a source of arginine and a composition comprising Rose hip and/or extracts thereof consisting of glycosides of mono- or diacylglycerol compounds, and/or *Quercus robur*) which may be taken as a single daily administration or by multiple small doses taken over the course of a day.

Also encompassed is a kit comprising the preparation of the invention or the composition of the invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Example 1

Statistical Processing

Aim: a Single-Center, Randomized, Placebo-Controlled Study of Prelox® Lady, Effects on Emotional, Physical Health and Sexual Function in Pre-Menopausal Women Aged 40 to 50 Years.

Study Population

A total of 80 women aged 40 to 50 years were enrolled in the present study. A random number generator was used to randomize the participants in two equal groups, each comprised of 40 females. Patients in arm A were treated with Prelox® Lady, while those in arm B received placebo.

Methods

All statistical tests were performed by SPSS 17.0.1. computer software. A probability of 0.05 rejected the null hypothesis and was considered significant. The following statistical methods were used:

1. Descriptive analysis
2. Graphical analysis
3. Variat analysis
4. Shapiro-Wilk test for type of distribution
5. Student's t-test for two independent samples
6. Nonparametric Mann-Whitney test for two independent samples
7. Repeated measures ANOVAs
8. Student's t-test for two dependent samples
9. Nonparametric Friedman's test for several dependent samples
10. Nonparametric Wilcoxon test for two dependent samples Results The mean age of all participants was 45.41±2.37 years (range 40-50). As described in Table 1, patients receiving treatment and controles were adjusted to age and no significant difference was present according to height and weight. It is notable that compared to arm B, women in arm A had significantly lower BMI scores and highter values of sistolic and diastolic blood pressure (SBP and DBP). Nevertheless, considering these measures as absolute values, the differance between the two groups was not so evident.

TABLE 1

Comparative analysis of patients' baseline characteristics

| Parameter | Group A (Prelox ® Lady) (n = 40) | | Group B (placebo) (n = 40) | | p |
|---|---|---|---|---|---|
| | $\bar{X}$ | SD | $\bar{X}$ | SD | |
| Age (years) | 45.58 | 2.24 | 45.25 | 2.51 | 0.543 |
| Height (cm) | 168.75 | 4.62 | 167.58 | 3.61 | 0.209 |
| Weight (kg) | 71.13 | 4.26 | 71.90 | 4.07 | 0.319 |
| BMI (kg/m$^2$) | 24.96 | 0.59 | 25.58 | 0.61 | <0.001 |
| SBP (mmHg) | 128.13 | 3.87 | 124.00 | 3.95 | <0.001 |
| DBP (mmHg) | 81.63 | 3.28 | 80.25 | 1.10 | 0.009 |

All 80 participants (100%) included in the study were employed non-smokers.

Symptoms assessed were major menopausal symptoms such as: Depressive moods, Feelings of vertigo, Headache, Heart palpitation, Hot flashes, Joint pain, Loss of concentration, Nervousness/irritability, Profuse perspiration (Night sweats), Sleep disturbances.

The two groups were stratified according to the number of the visit and Kupperman's index was used to compare the results (table 2). Vertigo, Headache, Joint pain, Palpitation and Total score were significantly higher in arm A when assessed for the first time. The other parameters did not differ statistically between the two groups. During second assessment (visit 2) all parameters (exept for Vertigo and Palpitation) were significantly higher in arm B. In the end of the study (visit 3) only the parameter Palpitation was still more common among arm A participants. Vertigo was equally scored. The rest parameters were significantly higher in arm B.

TABLE 2

A comperative analysis of Kupperman's index by visit (for each group)

| Parameter | Visit 1 | | | | | Visit 2 | | | | | Visit 3 | | | | |
|---|---|---|---|---|---|---|---|---|---|---|---|---|---|---|---|
| | Arm A | | Arm B | | | Arm A | | Arm B | | | Arm A | | Arm B | | |
| | $\bar{x}$ | SD | $\bar{X}$ | SD | p | $\bar{x}$ | SD | $\bar{X}$ | SD | p | $\bar{x}$ | SD | $\bar{X}$ | SD | p |
| Hot flashes | 7.90 | 0.63 | 8.00 | 0.00 | 0.317 | 4.30 | 1.07 | 8.00 | 0.00 | <0.001 | 4.00 | 0.00 | 8.00 | 0.00 | <0.001 |
| Night sweats | 3.95 | 0.32 | 4.00 | 0.00 | 0.317 | 2.15 | 0.53 | 4.00 | 0.00 | <0.001 | 2.00 | 0.00 | 4.00 | 0.00 | <0.001 |
| Sleep problems | 3.95 | 0.32 | 4.00 | 0.00 | 0.317 | 2.15 | 0.53 | 4.00 | 0.00 | <0.001 | 2.00 | 0.00 | 4.00 | 0.00 | <0.001 |
| Irritability | 3.95 | 0.32 | 4.00 | 0.00 | 0.317 | 2.05 | 0.32 | 3.95 | 0.32 | <0.001 | 2.00 | 0.00 | 4.00 | 0.00 | <0.001 |
| Depressed mood | 1.93 | 0.35 | 1.98 | 0.16 | 0.393 | 1.10 | 0.30 | 1.83 | 0.38 | <0.001 | 1.00 | 0.00 | 1.68 | 0.47 | <0.001 |
| Memory (concentration) | 1.83 | 0.50 | 1.88 | 0.33 | 0.533 | 0.98 | 0.36 | 1.73 | 0.45 | <0.001 | 0.95 | 0.22 | 1.55 | 0.60 | <0.001 |
| Vertigo (dizziness) | 1.53 | 0.60 | 1.20 | 0.56 | 0.010 | 0.65 | 0.53 | 0.68 | 0.73 | 0.868 | 0.28 | 0.45 | 0.53 | 0.72 | 0.139 |
| Headache | 1.88 | 0.33 | 1.60 | 0.50 | 0.005 | 0.98 | 0.16 | 1.45 | 0.55 | <0.001 | 0.93 | 0.27 | 1.35 | 0.53 | <0.001 |
| Backache/ limb pain | 1.83 | 0.38 | 1.55 | 0.50 | 0.008 | 0.98 | 0.16 | 1.43 | 0.50 | <0.001 | 0.95 | 0.22 | 1.20 | 0.56 | <0.009 |
| Palpitation | 1.65 | 0.53 | 1.15 | 0.53 | <0.001 | 0.78 | 0.42 | 0.73 | 0.51 | 0.581 | 0.65 | 0.48 | 0.30 | 0.46 | 0.002 |
| Total score | 30.38 | 2.56 | 29.35 | 1.99 | 0.006 | 16.10 | 1.92 | 27.78 | 2.22 | <0.001 | 14.75 | 0.95 | 26.60 | 1.98 | <0.001 |

Comperative analysis of Kupperman's index for each visit by group.

As described in table 3, arm A patients had already shown a significant improvement of all parameters (exept for Night sweats, Sleep problems and Irritability) by the time of the second visit. This tendency was present until the end of the study for the parameters Depressed mood, Vertigo and Total Score. Control group patient variables Hot flashes, Night sweats, Sleep problems and Irritability remained unchanged for the whole period of observation. Despite the administration of placebo, in the interval between visit 2 and visit 3, women in arm B demonstated a decrease in all parameters remaining (only Vertigo score was the same). This is well demonstrated in FIG. 1, where three groups of complaints could be delineated. Women in both groups most frequent complaints were Hot flashes, Night sweats, Sleep problems and Irritability. These are also the symptoms, which improved only in arm A. Second most reported events were Depressed mood, Loss of concentration, Headache and Backache/limb pain, which were posivitely influenced in both groups, but that was more notable in arm A. The less prevalent parameters reported were Vertigo, which decreased its score in both groups and Palpitation, which actually improved more distinctly in the placebo group.

TABLE 3

A comparative analysis of Kupperman's index for each visit by group

| | Arm A | | | | | | Arm B | | | | | |
|---|---|---|---|---|---|---|---|---|---|---|---|---|
| | Visit 1 | | Visit 2 | | Visit 3 | | Visit 1 | | Visit 2 | | Visit 3 | |
| Parameter | $\bar{x}$ | SD | $\bar{x}$ | SD | $\bar{x}$ | SD | $\bar{x}$ | SD | $\bar{x}$ | SD | $\bar{x}$ | SD |
| Hot flashes | $7.90^a$ | 0.63 | $4.30^b$ | 1.07 | $4.00^b$ | 0.00 | $8.00^a$ | 0.00 | $8.00^a$ | 0.00 | $8.00^a$ | 0.00 |
| Night sweats | $3.95^a$ | 0.32 | $2.15^a$ | 0.53 | $2.00^b$ | 0.00 | $4.00^a$ | 0.00 | $4.00^a$ | 0.00 | $4.00^a$ | 0.00 |
| Sleep problems | $3.95^a$ | 0.32 | $2.15^a$ | 0.53 | $2.00^b$ | 0.00 | $4.00^a$ | 0.00 | $4.00^a$ | 0.00 | $4.00^a$ | 0.00 |
| Irritability | $3.95^a$ | 0.32 | $2.05^a$ | 0.32 | $2.00^b$ | 0.00 | $4.00^a$ | 0.00 | $3.95^a$ | 0.32 | $4.00^a$ | 0.00 |
| Depressed mood | $1.93^a$ | 0.35 | $1.10^b$ | 0.30 | $1.00^c$ | 0.00 | $1.98^a$ | 0.16 | $1.83^b$ | 0.38 | $1.68^c$ | 0.47 |
| Memory (concentration) | $1.83^a$ | 0.50 | $0.98^b$ | 0.36 | $0.95^b$ | 0.22 | $1.88^a$ | 0.33 | $1.73^b$ | 0.45 | $1.55^c$ | 0.60 |
| Vertigo (dizziness) | $1.53^a$ | 0.60 | $0.65^b$ | 0.53 | $0.28^c$ | 0.45 | $1.20^a$ | 0.56 | $0.68^b$ | 0.73 | $0.53^b$ | 0.72 |
| Headache | $1.88^a$ | 0.33 | $0.98^b$ | 0.16 | $0.93^b$ | 0.27 | $1.60^a$ | 0.50 | $1.45^b$ | 0.55 | $1.35^c$ | 0.53 |
| Backache/limb pain | $1.83^a$ | 0.38 | $0.98^b$ | 0.16 | $0.95^b$ | 0.22 | $1.55^a$ | 0.50 | $1.43^b$ | 0.50 | $1.20^c$ | 0.56 |
| Palpitation | $1.65^a$ | 0.53 | $0.78^b$ | 0.42 | $0.65^b$ | 0.48 | $1.15^a$ | 0.53 | $0.73^b$ | 0.51 | $0.30^c$ | 0.46 |
| Total score | $30.38^a$ | 2.56 | $16.10^b$ | 1.92 | $14.75^c$ | 0.95 | $29.35^a$ | 1.99 | $27.78^b$ | 2.22 | $26.60^c$ | 1.98 |

\*Unchanged letter stands for statistical insignificance (a – a)
\*\*A different letter means presence of statistically significant difference (p < 0.05) (a – b, b – c)

Figure 2:
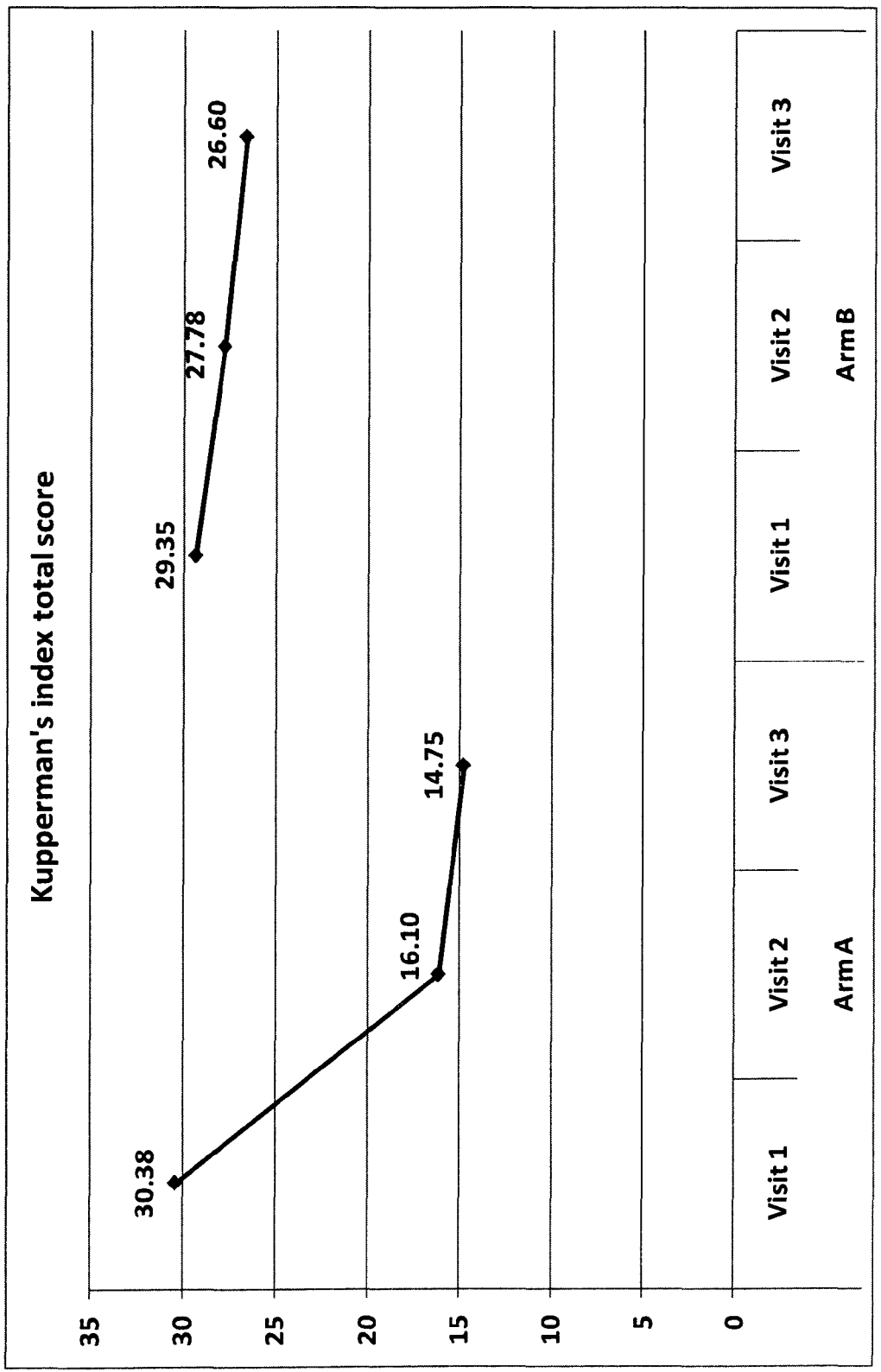
FIG. 2. Shows a comparative analysis of Kupperman's index total score for each visit by group.

Kupperman's index total score was also dinamically changed visit-by-visit and in both groups (FIG. 2). According to total score alleviation of climacteric symptoms was more pronounced in arm A. At the same time, total scores in arm B also decreased permenantely until the end of the observation.

Figure 3:
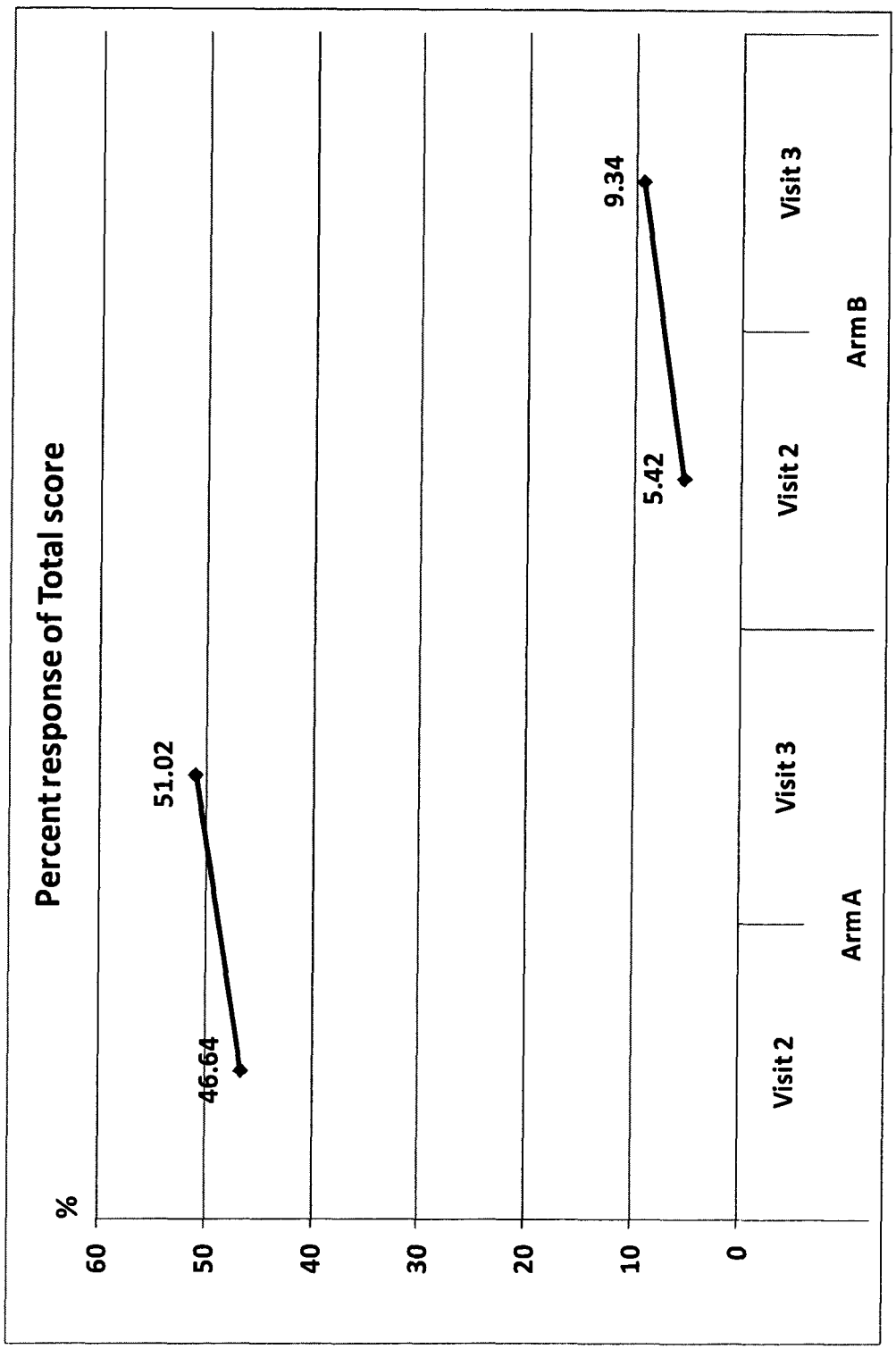
FIG. 3. Illustrates a comparative analysis of the percent response to Total score between visit 2 and visit 3 for each group.

Additionaly, table 4 and 5 show that the percentage of women who had benefit from the treatment was much higher in arm A in comparison to arm B and that trend was obvious not only during the second, but also during the third visit. Also, in both groups, the percentage of women reporting relief in their symptoms was significantly higher the third time, compared to the second time. These results are further supported by FIG. 3.

TABLE 4

A comparative analysis of the percent response to treatment according to total score in arm A and arm B for visit 2 and visit 3

| | Visit 2 | | | | | Visit 3 | | | | |
|---|---|---|---|---|---|---|---|---|---|---|
| | Arm A | | Arm B | | | Arm A | | Arm B | | |
| Parameter | $\bar{x}$ | SD | $\bar{x}$ | SD | p | $\bar{x}$ | SD | $\bar{x}$ | SD | p |
| Percent response of Total score | 46.64 | 7.59 | 5.42 | 2.80 | <0.001 | 51.02 | 6.14 | 9.34 | 3.61 | <0.001 |

TABLE 5

A comparative analysis of the percent response to treatment according to total score between visit 2 and visit 3 for each group

| | Arm A | | | | | Arm B | | | | |
|---|---|---|---|---|---|---|---|---|---|---|
| | Visit 2 | | Visit 3 | | | Visit 2 | | Visit 3 | | |
| Parameter | $\bar{x}$ | SD | $\bar{x}$ | SD | p | $\bar{x}$ | SD | $\bar{x}$ | SD | p |
| Percent response of Total score | 46.64 | 7.59 | 51.02 | 6.14 | <0.001 | 5.42 | 2.80 | 9.34 | 3.61 | <0.001 |

The degree of severity of climacteric symptoms reported in the two groups was analysed for each visit independently. As table 6 demonstrates, during the first visit both women in arm A and arm B graded the severity of their complaints as moderate (range 20-34). At the time of the second and the third visit, significant variations in the degree of severity of climacteric symptoms occurred (between the two groups).

TABLE 6

A comparative analysis of the severity of climacteric symptoms in arm A and arm B by visit.

| | Visit 1 | | | | | Visit 2 | | | | | Visit 3 | | | | |
|---|---|---|---|---|---|---|---|---|---|---|---|---|---|---|---|
| | Arm A | | Arm B | | | Arm A | | Arm B | | | Arm A | | Arm B | | |
| Parameter | % | Sp | % | Sp | p | % | Sp | % | Sp | p | % | Sp | % | Sp | p |
| Minor discomfort (1-14) | 0 | 0 | 0 | 0 | n.s. | 15.00 | 5.65 | 0 | 0 | <0.05 | 32.50 | 7.41 | 0 | 0 | <0.05 |
| Little discomfort (15-19) | 0 | 0 | 0 | 0 | n.s. | 80.00 | 6.32 | 0 | 0 | <0.05 | 67.50 | 7.41 | 0 | 0 | <0.05 |
| Clear (moderate) discomfort (20-34) | 100 | 0 | 100 | 0 | n.s. | 5.00 | 3.45 | 100 | 0 | <0.05 | 0 | 0 | 100 | 0 | <0.05 |

Figure 4:
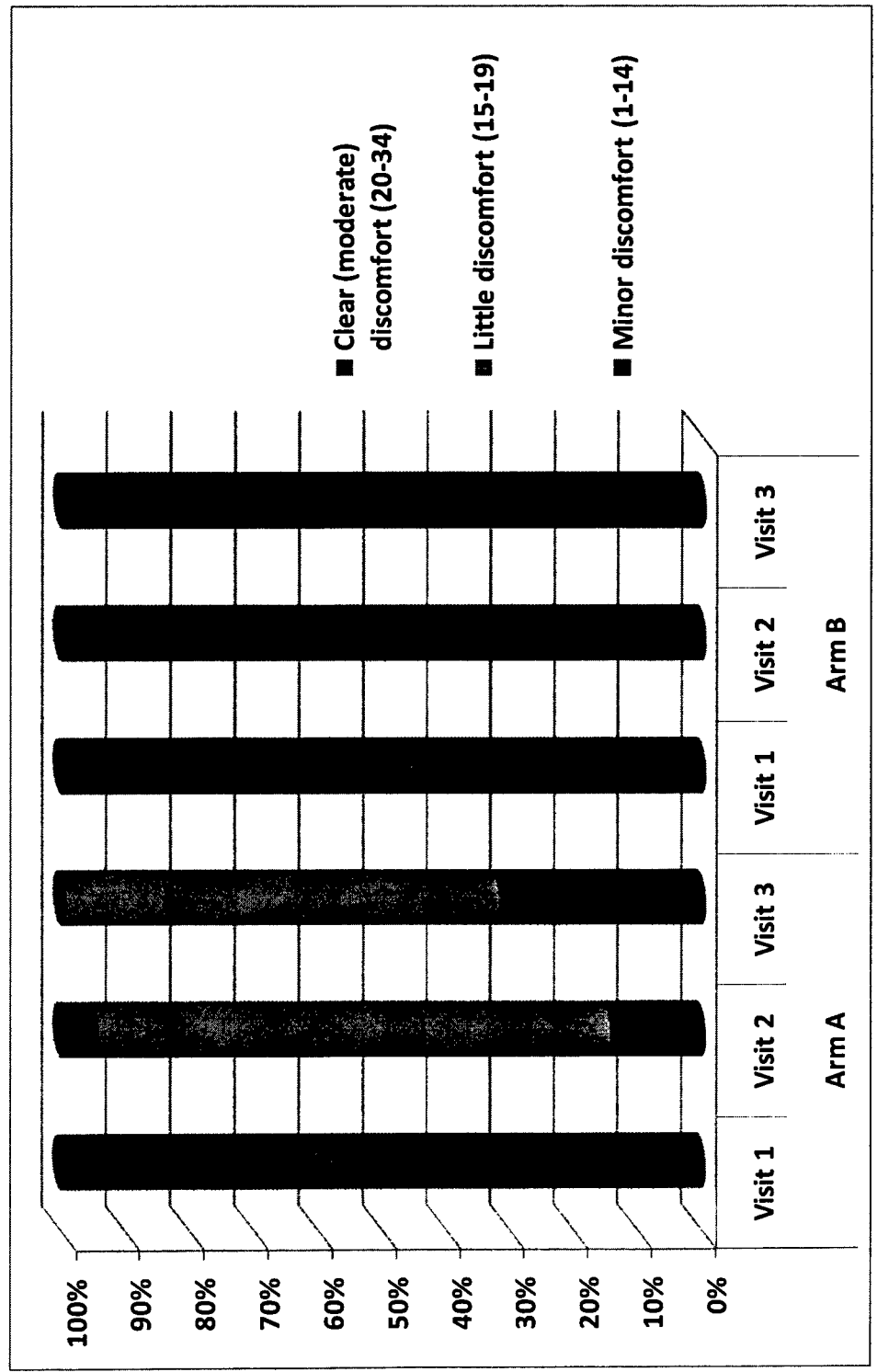
FIG. 4. Shows a comparative analysis of the severity of climacteric symptoms for each visit, by group.

A comparative analysis of the severity of climacteric symptoms by visit is shown in table 7. It demonstrates how severity of symptoms reported in arm B kept a permanent level during the whole period of examination, while participants in the treatment arm experienced a pronounced improvement of their symptoms. That is well illustrated in FIG. 4 where the following most important issues are implaied—when the observation began (visit1) 100% of the women in the treatment arm defined their symptoms as moderate, then, on the second assessment, this category was nearly fully replaced by the lower category—little (mild) discomfort (score 15-19) and even the lowest category—minor discomfort (1-14) was present. By the time of the last visit, no participant had moderate discomfort, little (mild) discomfort remained the most prevalent one and a significant increase in minor discomfort was noted.

TABLE 7

A comparative analysis of the severity of climacteric symptoms for each visit, by group

| | Arm A | | | | | | Arm B | | | | | |
|---|---|---|---|---|---|---|---|---|---|---|---|---|
| | Visit 1 | | Visit 2 | | Visit 3 | | Visit 1 | | Visit 2 | | Visit 3 | |
| Parameter | % | Sp | % | Sp | % | Sp | % | Sp | % | Sp | % | Sp |
| Minor discomfort (1-14) | $0^a$ | 0 | $15.00^b$ | 5.65 | $32.50^b$ | 7.41 | $0^a$ | 0 | $0^a$ | 0 | $0^a$ | 0 |
| Little discomfort (15-19) | $0^a$ | 0 | $80.00^b$ | 6.32 | $67.50^b$ | 7.41 | $0^a$ | 0 | $0^a$ | 0 | $0^a$ | 0 |
| Clear (moderate) discomfort (20-34) | $100^a$ | 0 | $5.00^b$ | 3.45 | $0^b$ | 0 | $100^a$ | 0 | $100^a$ | 0 | $100^a$ | 0 |

*Unchanged letter stands for statistical insignificance (a – a)
**A different letter means presence of statistically significant difference (p < 0.05) (a – b, b – c)

Climacteric symptoms were additionally evaluated by the Women's Health Questionnaire (WHQ). It comprises 36 symptoms and signs, rated on a 4-point scale, including: somatic symptoms, depressed mood, cognitive difficulties, anxiety and fear, sexual functioning, vasomotor symptoms, sleep problems, menstrual problems, and self-perceived attraction. It provides individual dimensions and overall scores. The higher the score, the more pronounced the suffering and dysfunction.

A comparative analysis of the presence of climacteric symptoms, assessed by the Women's Health Questionnaire (WHQ) was done independently for each group by visit (table 8). During the first visit women in arm A presented with significantly higher scores of all WHQ symptoms, compared to women in arm B. Only one complaint was more prevalent among patients in the placebo group and that were the signs of somatic symptoms. During the observation period (visit 2 and 3) absolutely all WHQ symptoms were downgraded more notably in arm A compared to arm B.

A comparative analysis of WHQ symptoms by visit is shown in table 9.

All WHQ symptoms diminished during the observation period in both groups but that tendency was less pronounced in arm B.

Figure 5:
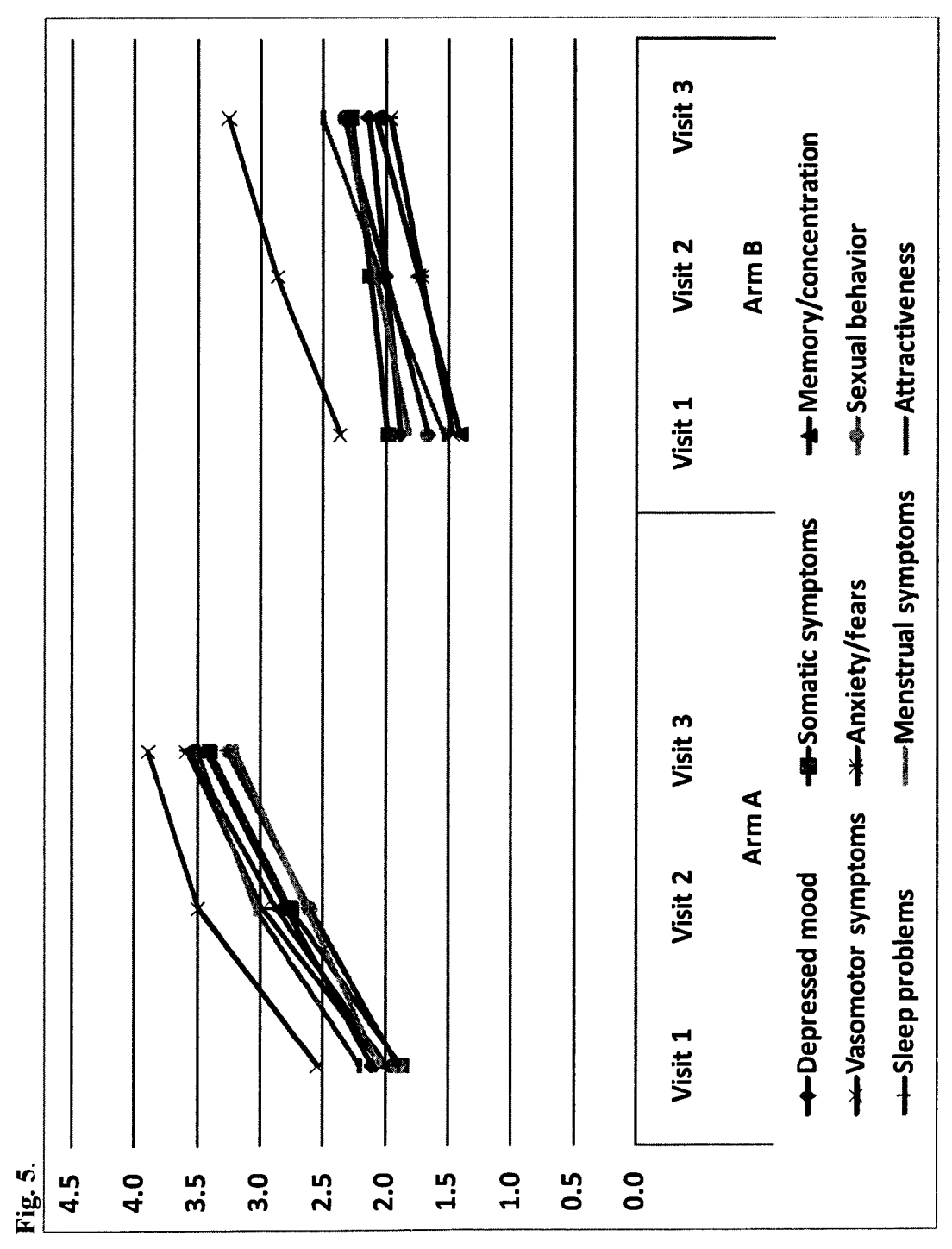

Results shown in table 8 and 9 are graphically illustrated in FIG. 5. It demonstrates that the most common complaint reported by participants from both groups was the presence of vasomotor symptoms. All other symptoms were rated and presented in a similar way in the two groups.

TABLE 8

A comparative analysis of WHQ symptoms in arm A and arm B by visit

|  | Visit 1 | | | | | Visit 2 | | | | | Visit 3 | | | | |
|---|---|---|---|---|---|---|---|---|---|---|---|---|---|---|---|
|  | Arm A | | Arm B | | | Arm A | | Arm B | | | Arm A | | Arm B | | |
| Parameter | $\bar{x}$ | SD | $\bar{X}$ | SD | p | $\bar{x}$ | SD | $\bar{X}$ | SD | p | $\bar{x}$ | SD | $\bar{X}$ | SD | p |
| Depressed mood | 2.10 | 0.15 | 1.88 | 0.09 | <0.001 | 2.79 | 0.15 | 2.00 | 0.09 | <0.001 | 3.43 | 0.17 | 2.13 | 0.09 | <0.001 |
| Somatic symptoms | 1.87 | 0.12 | 1.98 | 0.12 | 0.001 | 2.75 | 0.15 | 2.12 | 0.11 | <0.001 | 3.40 | 0.15 | 2.27 | 0.12 | <0.001 |
| Memory/concentration | 1.99 | 0.16 | 1.41 | 0.14 | <0.001 | 2.86 | 0.26 | 1.74 | 0.14 | <0.001 | 3.57 | 0.16 | 2.07 | 0.14 | <0.001 |
| Vasomotor symptoms | 2.54 | 0.21 | 2.36 | 0.63 | <0.001 | 3.49 | 0.08 | 2.86 | 0.63 | <0.001 | 3.89 | 0.21 | 3.25 | 0.42 | <0.001 |
| Anxiety/fears | 2.02 | 0.12 | 1.46 | 0.13 | <0.001 | 2.98 | 0.18 | 1.71 | 0.13 | <0.001 | 3.58 | 0.14 | 1.96 | 0.13 | <0.001 |
| Sexual behaviour | 1.90 | 0.15 | 1.66 | 0.23 | <0.001 | 2.60 | 0.19 | 2.00 | 0.22 | <0.001 | 3.24 | 0.15 | 2.33 | 0.23 | <0.001 |
| Sleep problems | 1.90 | 0.15 | 1.66 | 0.23 | <0.001 | 2.61 | 0.20 | 2.00 | 0.22 | <0.001 | 3.26 | 0.19 | 2.33 | 0.23 | <0.001 |
| Menstrual symptoms | 2.04 | 0.11 | 1.82 | 0.27 | <0.001 | 2.63 | 0.24 | 2.07 | 0.27 | <0.001 | 3.19 | 0.24 | 2.32 | 0.27 | <0.001 |
| Attractiveness | 2.20 | 0.25 | 1.53 | 0.11 | <0.001 | 3.03 | 0.11 | 2.03 | 0.11 | <0.001 | 3.50 | 0.00 | 2.50 | 0.16 | <0.001 |

TABLE 9

A comparative analysis of WHQ symptoms for each visit by group

|  | Arm A | | | | | | Arm B | | | | | |
|---|---|---|---|---|---|---|---|---|---|---|---|---|
|  | Visit 1 | | Visit 2 | | Visit 3 | | Visit 1 | | Visit 2 | | Visit 3 | |
| Parameter | $\bar{x}$ | SD | $\bar{x}$ | SD | $\bar{x}$ | SD | $\bar{x}$ | SD | $\bar{x}$ | SD | $\bar{x}$ | SD |
| Depressed mood | $2.10^a$ | 0.15 | $2.79^b$ | 0.15 | $3.43^c$ | 0.17 | $1.88^a$ | 0.09 | $2.00^b$ | 0.09 | $2.13^c$ | 0.09 |
| Somatic symptoms | $1.87^a$ | 0.12 | $2.75^b$ | 0.15 | $3.40^c$ | 0.15 | $1.98^a$ | 0.12 | $2.12^b$ | 0.11 | $2.27^c$ | 0.12 |
| Memory/concentration | $1.99^a$ | 0.16 | $2.86^b$ | 0.26 | $3.57^c$ | 0.16 | $1.41^a$ | 0.14 | $1.74^b$ | 0.14 | $2.07^c$ | 0.14 |
| Vasomotor symptoms | $2.54^a$ | 0.21 | $3.49^b$ | 0.08 | $3.89^c$ | 0.21 | $2.36^a$ | 0.63 | $2.86^b$ | 0.63 | $3.25^c$ | 0.42 |
| Anxiety/fears | $2.02^a$ | 0.12 | $2.98^b$ | 0.18 | $3.58^c$ | 0.14 | $1.46^a$ | 0.13 | $1.71^b$ | 0.13 | $1.96^c$ | 0.13 |
| Sexual behavior | $1.90^a$ | 0.15 | $2.60^b$ | 0.19 | $3.24^c$ | 0.15 | $1.66^a$ | 0.23 | $2.00^b$ | 0.22 | $2.33^c$ | 0.23 |
| Sleep problems | $1.90^a$ | 0.15 | $2.61^b$ | 0.20 | $3.26^c$ | 0.19 | $1.66^a$ | 0.23 | $2.00^b$ | 0.22 | $2.33^c$ | 0.23 |
| Menstrual symptoms | $2.04^a$ | 0.11 | $2.63^b$ | 0.24 | $3.19^c$ | 0.24 | $1.82^a$ | 0.27 | $2.07^b$ | 0.27 | $2.32^c$ | 0.27 |
| Attractiveness | $2.20^a$ | 0.25 | $3.03^b$ | 0.11 | $3.50^c$ | 0.00 | $1.53^a$ | 0.11 | $2.03^b$ | 0.11 | $2.50^c$ | 0.16 |

*Unchanged letter stands for statistical insignificance (a – a)
**A different letter means presence of statistically significant difference (p < 0.05) (a – b, b – c)

Data in table 8 and table 9 correlates with the percent response to treatment of the examined population.

Response to treatment evaluated as patients experiencing relief in their symptoms (%), was compared visit by visit for each group in table 10. Compared to arm B, a significantly higher percent of women in arm A responded to the treatment by the time of the second and the third assessment.

Table 11 demonstrates the dynamical increase in women, responding to the treatment (%), evaluated for each visit in both groups. Analyzing the results as relative numbers we could reveal a reliable increase of the % response to WHQ symptoms between the second and the third visit for both groups. Also, the dynamics of this evolution does not appear to differ statistically between the two groups. Nevertheless, translating the results as absolute values we would say that the response to treatment in arm A was superior (table 11).

TABLE 10

A comparative analysis of the percent response to WHQ symptoms in arm A and arm B by visit (visits 2 and 3)

|  | Visit 2 | | | | | Visit 3 | | | | |
|---|---|---|---|---|---|---|---|---|---|---|
|  | Arm A | | Arm B | | | Arm A | | Arm B | | |
| Parameter | $\bar{x}$ | SD | $\bar{X}$ | SD | p | $\bar{x}$ | SD | $\bar{X}$ | SD | p |
| Depressed mood | 33.14 | 8.00 | 6.67 | 0.42 | <0.001 | 63.78 | 11.26 | 13.34 | 0.64 | <0.001 |
| Somatic symptoms | 46.74 | 3.92 | 7.00 | 1.35 | <0.001 | 81.93 | 7.94 | 14.39 | 1.02 | <0.001 |
| Memory/concentration | 43.78 | 12.19 | 23.71 | 2.16 | <0.001 | 80.25 | 16.54 | 47.93 | 4.59 | <0.001 |
| Vasomotor symptoms | 38.21 | 10.02 | 22.34 | 4.53 | <0.001 | 53.92 | 11.69 | 41.46 | 14.99 | <0.001 |
| Anxiety/fears | 47.83 | 7.20 | 17.30 | 1.56 | <0.001 | 77.50 | 9.61 | 34.60 | 3.13 | <0.001 |
| Sexual behaviour | 37.05 | 6.01 | 20.69 | 3.10 | <0.001 | 70.94 | 7.50 | 40.88 | 5.89 | <0.001 |
| Sleep problems | 37.47 | 6.31 | 20.69 | 3.10 | <0.001 | 72.20 | 8.06 | 41.03 | 5.80 | <0.001 |
| Menstrual symptoms | 28.72 | 13.01 | 14.02 | 1.93 | <0.001 | 56.15 | 11.48 | 28.04 | 3.86 | <0.001 |
| Attractiveness | 39.13 | 15.60 | 32.92 | 1.84 | 0.038 | 61.00 | 17.36 | 64.17 | 8.05 | 0.048 |

TABLE 11

A comparative analysis of the percent response to WHQ symptoms for visit 2 and visit 3 by group

| | Arm A | | | | | Arm B | | | | |
|---|---|---|---|---|---|---|---|---|---|---|
| | Visit 2 | | Visit 3 | | | Visit 2 | | Visit 3 | | |
| Parameter | x̄ | SD | X̄ | SD | p | x̄ | SD | X̄ | SD | p |
| Depressed mood | 33.14 | 8.00 | 63.78 | 11.26 | <0.001 | 6.67 | 0.42 | 13.34 | 0.64 | <0.001 |
| Somatic symptoms | 46.74 | 3.92 | 81.93 | 7.94 | <0.001 | 7.00 | 1.35 | 14.39 | 1.02 | <0.001 |
| Memory/concentration | 43.78 | 12.19 | 80.25 | 16.54 | <0.001 | 23.71 | 2.16 | 47.93 | 4.59 | <0.001 |
| Vasomotor symptoms | 38.21 | 10.02 | 53.92 | 11.69 | <0.001 | 22.34 | 4.53 | 41.46 | 14.99 | <0.001 |
| Anxiety/fears | 47.83 | 7.20 | 77.50 | 9.61 | <0.001 | 17.30 | 1.56 | 34.60 | 3.13 | <0.001 |
| Sexual behaviour | 37.05 | 6.01 | 70.94 | 7.50 | <0.001 | 20.69 | 3.10 | 40.88 | 5.89 | <0.001 |
| Sleep problems | 37.47 | 6.31 | 72.20 | 8.06 | <0.001 | 20.69 | 3.10 | 41.03 | 5.80 | <0.001 |
| Menstrual symptoms | 28.72 | 13.01 | 56.15 | 11.48 | <0.001 | 14.02 | 1.93 | 28.04 | 3.86 | <0.001 |
| Attractiveness | 39.13 | 15.60 | 61.00 | 17.36 | <0.001 | 32.92 | 1.84 | 64.17 | 8.05 | <0.001 |

*Unchanged letter stands for statistical insignificance (a – a)
**A different letter means presence of statistically significant difference ($p < 0.05$) (a – b, b – c)

Figure 6:
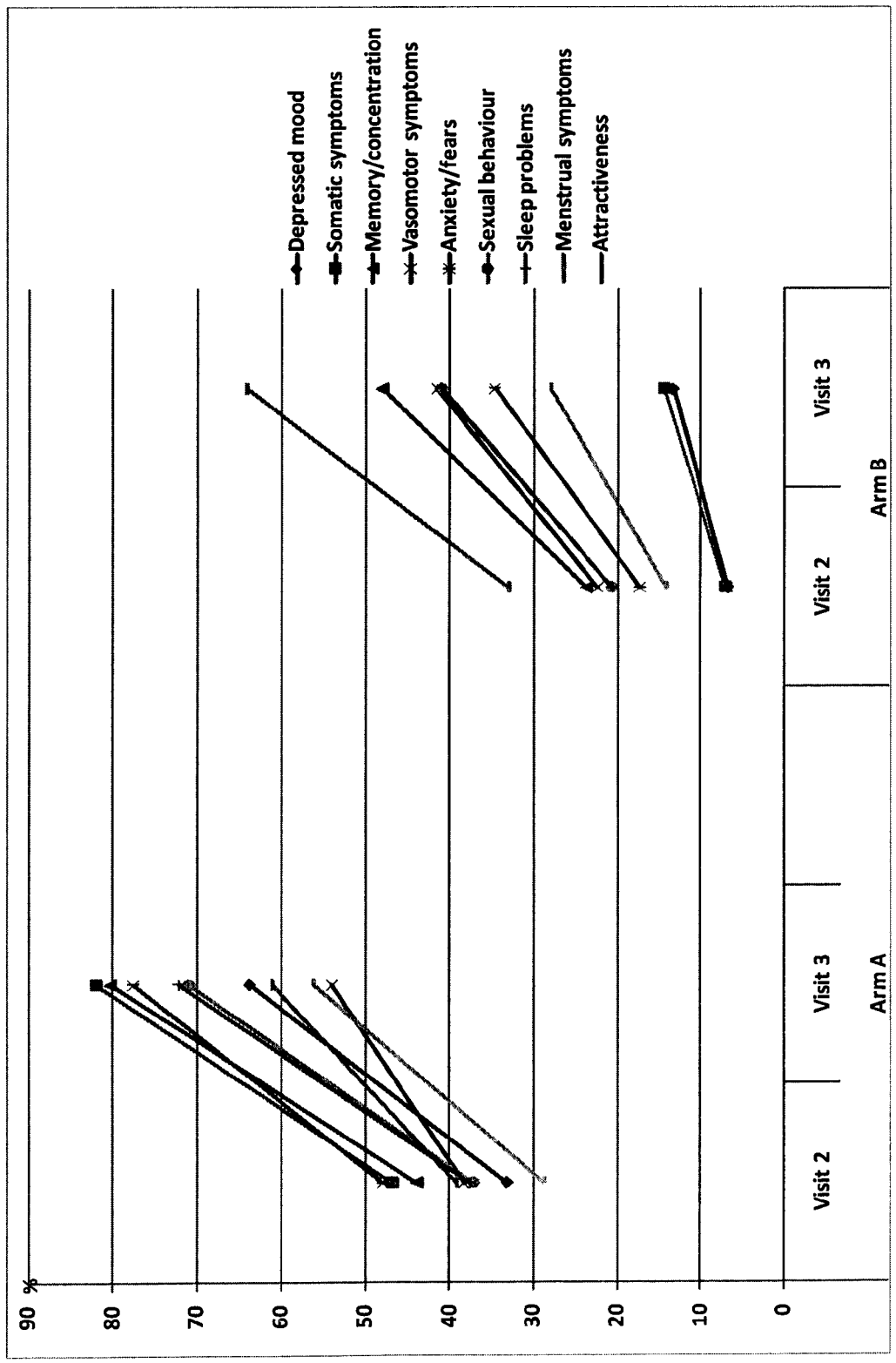
FIG. 6. Shows a comparative analysis of % response to WHQ symptoms for visit 2 and visit 3 by group.

In FIG. 6 some basic issues could be further outlined. Women in the placebo arm had lower percent of response to therapy, compared to women in the treatment arm. Interestingly, the symptom most influenced by the administration of placebo, was the self-perceived attraction. Also in arm B, the symptoms less reduced by the end of the study, were depressed mood and somatic symptoms. What makes an impression is that, together with menstrual problems, feeling of depression was similarly stable in arm A. Women in arm A had the highest percent of response to the symptoms loss of concentration, anxiety/fears and somatic symptoms.

The Female Sexual Function Index (FSFI) was used to assess sexual function in women.

The FSFI is a brief, 19-item self-report measure of female sexual function that provides scores on six domains of sexual function as well as a total score. Researchers have confirmed the following domains: desire (2 items), arousal (4 items), lubrication (4 items), orgasm (3 items), satisfaction (3 items), and pain (3 items).

A comparative analysis of FSFI domain scores and full scale scores for arm A and arm B is presented in table 12. All FSFI domain scores and full scale scores were significantly higher in the treatment arm compared to the placebo arm and that was well demonstrated for each visit.

A comparative analysis of FSFI domain scores and full scale scores visit by visit for arm A and arm B is shown in table 13. The dynamics of FSFI domain scores and full scale scores in the two groups is approximately the same—all values significantly increased during the whole study period. Only one domain—desire—did not change in arm B between the first and the second visit (table 13).

TABLE 12

A comparative analysis of FSFI domain scores and full scale scores visit for arm A and arm B by visit

| | Visit 1 | | | | | Visit 2 | | | | | Visit 3 | | | | |
|---|---|---|---|---|---|---|---|---|---|---|---|---|---|---|---|
| | Arm A | | Arm B | | | Arm A | | Arm B | | | Arm A | | Arm B | | |
| Parameter | x̄ | SD | X̄ | SD | p | x̄ | SD | X̄ | SD | p | x̄ | SD | X̄ | SD | p |
| Desire | 2.58 | 0.43 | 2.13 | 0.51 | <0.001 | 3.50 | 0.54 | 2.13 | 0.51 | <0.001 | 4.23 | 0.66 | 2.67 | 0.51 | <0.001 |
| Arousal | 2.85 | 0.59 | 2.13 | 0.51 | <0.001 | 3.72 | 0.53 | 2.40 | 0.00 | <0.001 | 4.47 | 0.62 | 2.67 | 0.51 | <0.001 |
| Lubrication | 2.85 | 0.59 | 2.13 | 0.51 | <0.001 | 3.72 | 0.53 | 2.40 | 0.00 | <0.001 | 4.53 | 0.62 | 2.76 | 0.56 | <0.001 |
| Orgasm | 2.85 | 0.59 | 2.13 | 0.51 | <0.001 | 3.69 | 0.57 | 2.40 | 0.00 | <0.001 | 4.46 | 0.64 | 2.73 | 0.54 | <0.001 |
| Satisfaction | 2.85 | 0.59 | 2.13 | 0.51 | <0.001 | 3.63 | 0.64 | 2.40 | 0.00 | <0.001 | 4.47 | 0.61 | 2.73 | 0.54 | <0.001 |
| Pain | 2.52 | 0.53 | 1.77 | 0.61 | <0.001 | 3.39 | 0.54 | 2.67 | 0.51 | <0.001 | 4.32 | 0.65 | 3.06 | 0.60 | <0.001 |
| Full Scale Score Range | 16.50 | 2.85 | 12.42 | 2.25 | <0.001 | 21.65 | 2.79 | 14.40 | 0.82 | <0.001 | 26.49 | 3.28 | 16.62 | 2.30 | <0.001 |

TABLE 13

A comparative analysis of FSFI domain scores and full scale scores visit by visit for arm A and arm B

| | Arm A | | | | | | Arm B | | | | | |
|---|---|---|---|---|---|---|---|---|---|---|---|---|
| | Visit 1 | | Visit 2 | | Visit 3 | | Visit 1 | | Visit 2 | | Visit 3 | |
| Parameter | x̄ | SD | x̄ | SD | x̄ | SD | x̄ | SD | x̄ | SD | x̄ | SD |
| Desire | 2.58[a] | 0.43 | 3.50[b] | 0.54 | 4.23[c] | 0.66 | 2.13[a] | 0.51 | 2.13[a] | 0.51 | 2.67[b] | 0.51 |
| Arousal | 2.85[a] | 0.59 | 3.72[b] | 0.53 | 4.47[c] | 0.62 | 2.13[a] | 0.51 | 2.40[b] | 0.00 | 2.67[c] | 0.51 |

TABLE 13-continued

A comparative analysis of FSFI domain scores and full scale scores visit by visit for arm A and arm B

| | Arm A | | | | | | Arm B | | | | | |
|---|---|---|---|---|---|---|---|---|---|---|---|---|
| | Visit 1 | | Visit 2 | | Visit 3 | | Visit 1 | | Visit 2 | | Visit 3 | |
| Parameter | $\bar{x}$ | SD | $\bar{x}$ | SD | $\bar{x}$ | SD | $\bar{x}$ | SD | $\bar{x}$ | SD | $\bar{x}$ | SD |
| Lubrication | $2.85^a$ | 0.59 | $3.72^b$ | 0.53 | $4.53^c$ | 0.62 | $2.13^a$ | 0.51 | $2.40^b$ | 0.00 | $2.76^c$ | 0.56 |
| Orgasm | $2.85^a$ | 0.59 | $3.69^b$ | 0.57 | $4.46^c$ | 0.64 | $2.13^a$ | 0.51 | $2.40^b$ | 0.00 | $2.73^c$ | 0.54 |
| Satisfaction | $2.85^a$ | 0.59 | $3.63^b$ | 0.64 | $4.47^c$ | 0.61 | $2.13^a$ | 0.51 | $2.40^b$ | 0.00 | $2.73^c$ | 0.54 |
| Pain | $2.52^a$ | 0.53 | $3.39^b$ | 0.54 | $4.32^c$ | 0.65 | $1.77^a$ | 0.61 | $2.67^b$ | 0.51 | $3.06^c$ | 0.60 |
| Full Scale Score Range | $16.50^a$ | 2.85 | $21.65^b$ | 2.79 | $26.49^c$ | 3.28 | $12.42^a$ | 2.25 | $14.40^b$ | 0.82 | $16.62^c$ | 2.30 |

Figure 7:
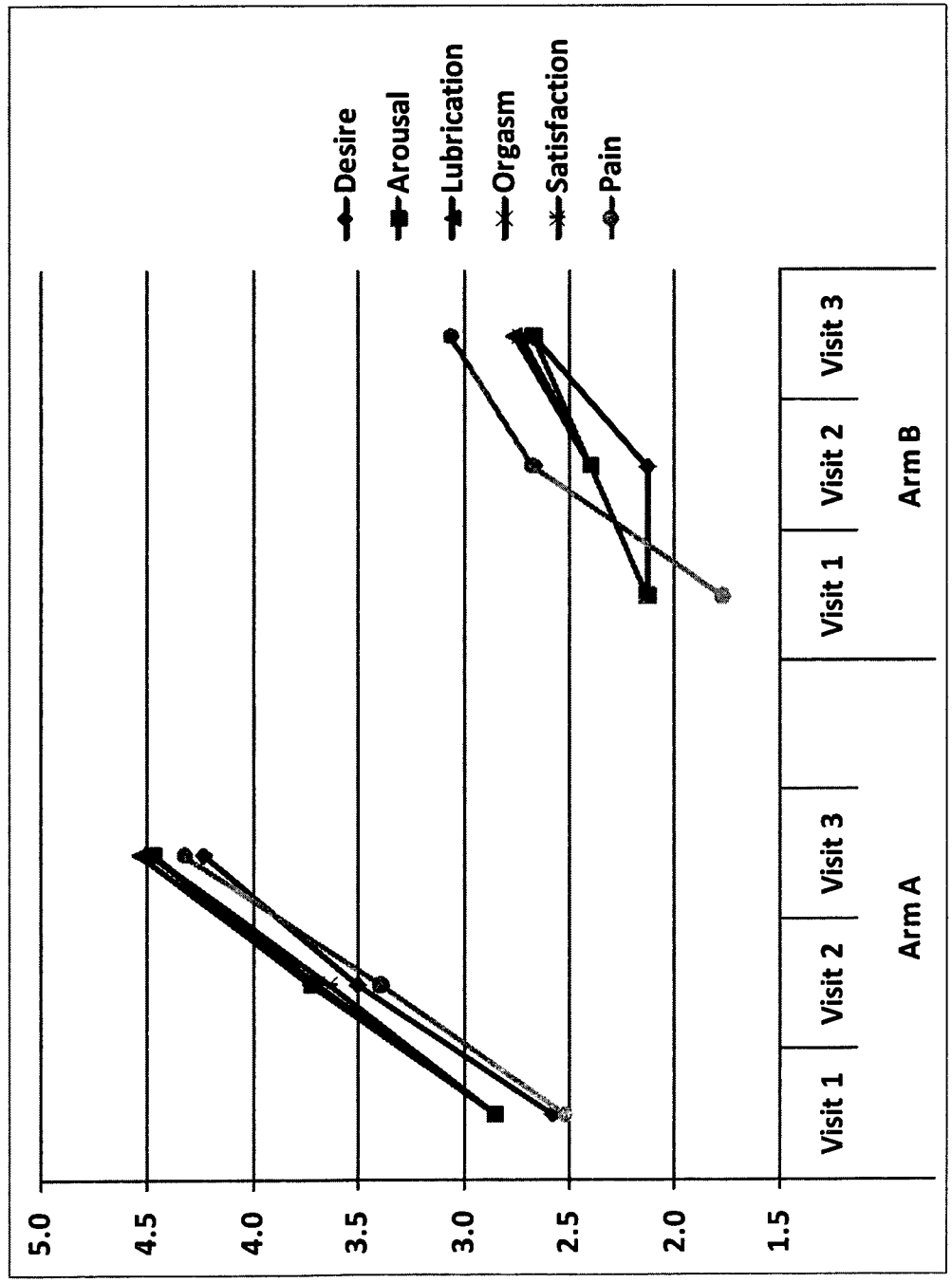
FIG. 7. Shows the dynamics of FSFI domain scores (mean values) for women in arm A and arm B.

Results from tables 12 and 13 are supported by the diagram in FIG. 7. In FIG. 7 one interesting phenomenon comes into focus-pain is the domain less relieved by the real medication (Prelox®Lady) and most influenced by the administration of placebo.

A comparative analysis of the % response to treatment, evaluated by the change of FSFI domain scores and full scale scores in the two groups by visit (table 14).

Analysis showed that the percent response to treatment was significantly higher in arm A, compared to arm B and that was present during second and third assessment (visit 2 and 3).

A comparative analysis of the % response to treatment, evaluated for each visit by the change of FSFI domain scores and full scale scores in the two groups (table 15).

Analyzing the results as relative numbers we could say that a reliable increase in the % response (evaluating FSFI domain scores and full scale scores) existed between the second and the third visit in both groups. Also, the dynamics of this evolution does not appear to differ statistically between the two groups. Nevertheless, translating the results as absolute values we would say that the response to treatment in arm A was superior (table 15).

TABLE 14

A comparative analysis of the % response to treatment, evaluated by the change of FSFI domain scores and full scale scores in the two groups by visit

| | Visit 2 | | | | | Visit 3 | | | | |
|---|---|---|---|---|---|---|---|---|---|---|
| | Arm A | | Arm B | | | Arm A | | Arm B | | |
| Parameter | $\bar{x}$ | SD | $\bar{X}$ | SD | p | $\bar{x}$ | SD | $\bar{X}$ | SD | p |
| Desire | 58.25 | 9.03 | 35.50 | 8.46 | <0.001 | 70.50 | 11.08 | 44.50 | 8.46 | <0.001 |
| Arousal | 62.00 | 8.83 | 40.00 | 0.00 | <0.001 | 74.50 | 10.30 | 44.50 | 8.46 | <0.001 |
| Lubrication | 62.00 | 8.83 | 40.00 | 0.00 | <0.001 | 75.50 | 10.37 | 46.00 | 9.28 | <0.001 |
| Orgasm | 61.50 | 9.49 | 40.00 | 0.00 | <0.001 | 74.33 | 10.63 | 45.50 | 9.04 | <0.001 |
| Satisfaction | 60.50 | 10.61 | 40.00 | 0.00 | <0.001 | 74.50 | 10.11 | 45.50 | 9.04 | <0.001 |
| Pain | 56.50 | 8.93 | 44.50 | 8.46 | <0.001 | 72.00 | 10.91 | 51.00 | 10.08 | <0.001 |
| Full Scale Score Range | 60.13 | 7.76 | 40.00 | 2.26 | <0.001 | 73.57 | 9.12 | 46.17 | 6.39 | <0.001 |

TABLE 15

A comparative analysis of the % response to treatment, evaluated for each visit by the change of FSFI domain scores and full scale scores in the two groups

| | Arm A | | | | | Arm B | | | | |
|---|---|---|---|---|---|---|---|---|---|---|
| | Visit 2 | | Visit 3 | | | Visit 2 | | Visit 3 | | |
| Parameter | $\bar{x}$ | SD | $\bar{X}$ | SD | p | $\bar{x}$ | SD | $\bar{X}$ | SD | p |
| Desire | 58.25 | 9.03 | 70.50 | 11.08 | <0.001 | 35.50 | 8.46 | 44.50 | 8.46 | <0.001 |
| Arousal | 62.00 | 8.83 | 74.50 | 10.30 | <0.001 | 40.00 | 0.00 | 44.50 | 8.46 | 0.003 |
| Lubrication | 62.00 | 8.83 | 75.50 | 10.37 | <0.001 | 40.00 | 0.00 | 46.00 | 9.28 | 0.001 |
| Orgasm | 61.50 | 9.49 | 74.33 | 10.63 | <0.001 | 40.00 | 0.00 | 45.50 | 9.04 | 0.001 |
| Satisfaction | 60.50 | 10.61 | 74.50 | 10.11 | <0.001 | 40.00 | 0.00 | 45.50 | 9.04 | 0.001 |
| Pain | 56.50 | 8.93 | 72.00 | 10.91 | <0.001 | 44.50 | 8.46 | 51.00 | 10.08 | 0.020 |
| Full Scale Score Range | 60.13 | 7.76 | 73.57 | 9.12 | <0.001 | 40.00 | 2.26 | 46.17 | 6.39 | <0.001 |

*Unchanged letter stands for statistical insignificance (a – a)
**A different letter means presence of statistically significant difference (p < 0.05) (a – b, b – c)

Figure 8:
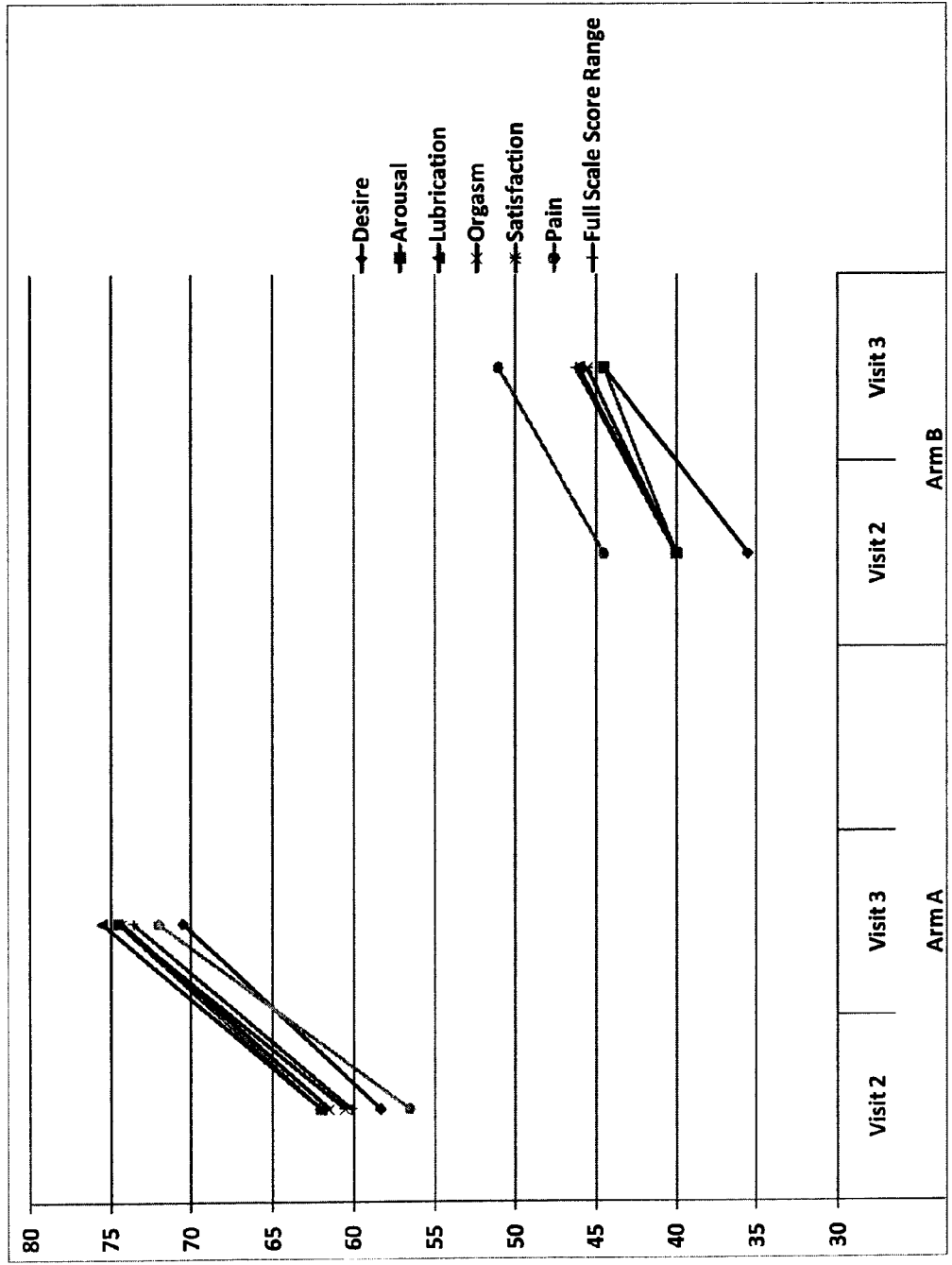
FIG. 8. Shows the dynamics of the % response to treatment (mean values), evaluated for each visit by the change of FSFI domain scores and full scale scores in the two groups.
Figure 9:
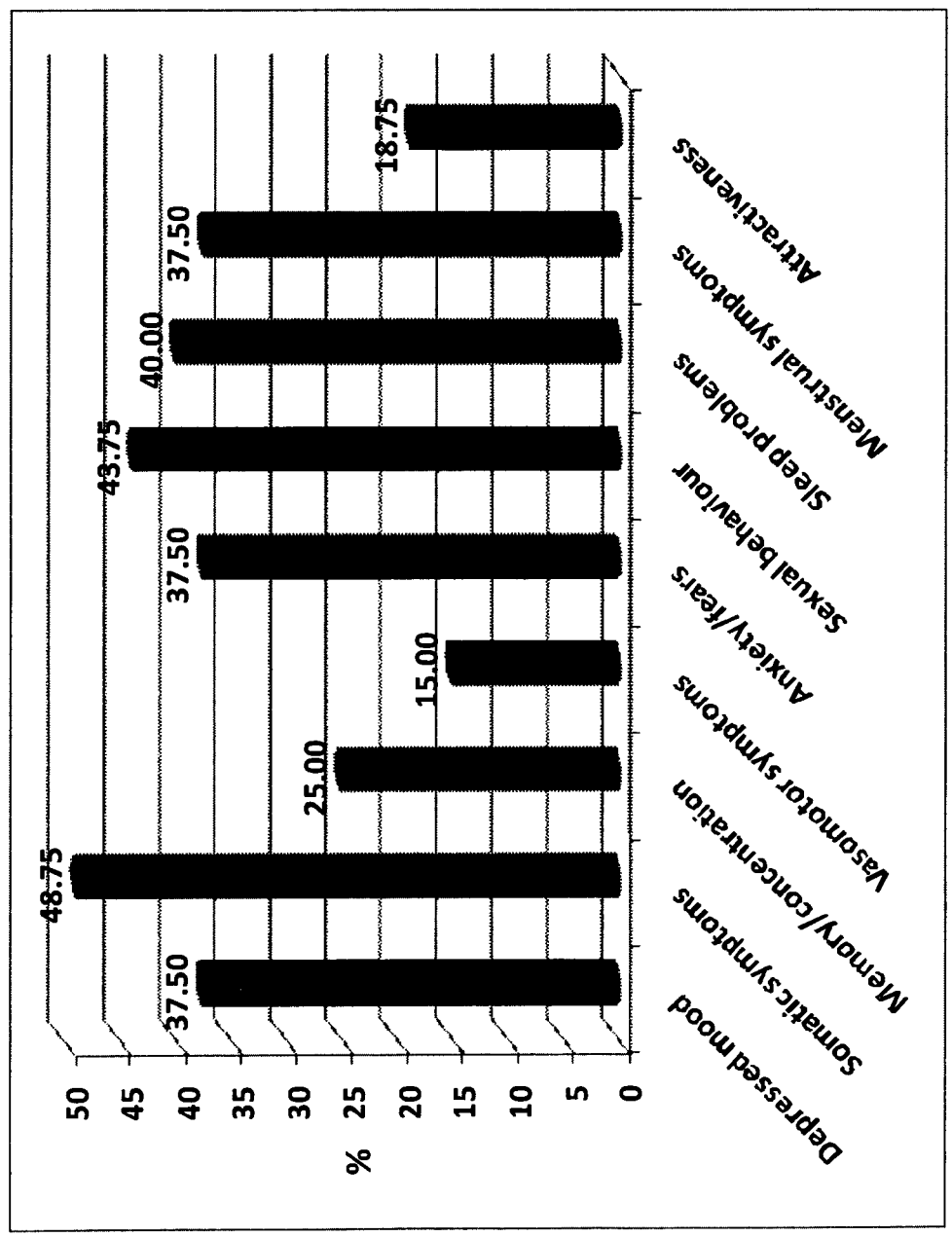
FIG. 9: Illustrates the profile of climacteric syndrome for Bulgarian women (n=80).

Some key findings are implied in FIG. 8:

Women in the placebo arm had lower percent of response to therapy, compared to women in the treatment arm. Interestingly, the symptom most influenced by the administration of placebo, was pain. The domains arousal and desire were improved the least in arm B. Treatment in arm A had the most possitive impact on the parameters orgasm and satisfaction, whereas desire and pain were influenced the least.

Conclusions

Our findings showed that women in both groups' most frequent complaints were Hot flashes, Night sweats, Sleep problems and Irritability. These are also the symptoms, which improved only in the treatment arm. According to total score alleviation of climacteric symptoms was more pronaunced in arm A. Severity of symptoms reported in arm B kept a permanent level during the whole period of examination, while participants in the treatment arm experienced a pronounced improvement of their symptoms and that was evident well before the end of the study. Blood pressure, BMI, lipid profile and TAC significantly improved in arm A. After the administration of Prelox®Lady a significant increase in hemoglobin concentration, erythrocytes, Hct, thrombocytes, prolactine, estradiol and testosterone and a decrease in leucocytes, fasting glucose and FSH were observed. Only LH and progesterone levels remained unchanged. Climacteric symptoms were additionally evaluated by the Women's Health Questionnaire (WHQ). During the observation period (visit 2 and 3) absolutely all WHQ symptoms were downgraded more notably in arm A compared to arm B. Prelox®Lady had a significant effect on improving concentration, anxiety/fears and somatic symptoms but failed to prevent depression. One of the symptoms less reduced in the placebo group was also the depressed mood. Interestingly, the symptom most influenced by the administration of placebo, was the self-perceived attraction. The Female Sexual Function Index (FSFI) was used to assess sexual function in women. One interesting phenomenon came into focus-pain was the domain less relieved by the real medication and most influenced by the administration of placebo. Treatment in arm A had the most possitive impact on the parameters orgasm and satisfaction, whereas desire and pain were influenced the least.

Example 2

Improvement of Sexual Function in Post-Menopausal Women

The aim of this study was to evaluate the efficacy of Prelox Lady® for improving/controlling sexual dysfunction (SD) in post-menopausal women with a healthy circulation.

Methods: The Prelox Lady® and control groups were comparable at inclusion with regard to the Female Sexual Function Index (FSFI) score with 36 women (50.1±3.1 years) and 39 women (51.2±2.3 years), respectively.

Results: After four weeks treatment there was a significant ($P<0.05$) improvement in the treatment group, which sustained until completion of the eight-week trial period. Minor, no significant changes were observed in controls. The median FSFI score at inclusion was 44.6 and significantly increased to 70.9 after four weeks and remained at this level after eight weeks (71.7; $P<0.05$ versus baseline). In the control group the total FSFI was 44.1 at inclusion, and reached 45.0 after four weeks and 47.4 after eight weeks, respectively. The treatment with Prelox Lady® was comparatively more effective than placebo ($P=0.022$).

Conclusion: This study opens an interesting perspective for women suffering from sexual function problems and suggests a promising new treatment option. Larger studies are required which should also investigate premenopausal and perimenopausal women.

Prelox Lady®, a registered trademark of Horphag Research, has been developed to improve women's quality of life and sexual function. This proprietary formulation consists of Pycnogenol, L-arginine, L-citrulline, and rose hip extract. Preliminary reports of exploratory investigations studies on L-arginine indicate a specific activity of Prelox Lady® in improving sensory effects in normal and diabetic subjects both by improving microangiopathy and neuropathy and by an important action of peripheral edema. L-arginine, as a precursor of nitric oxide (NO), has been used alone and in combination with several compounds to improve sexual function.

NO is the key mediator for the up-regulation of cyclic guanosine monophosphate (cGMP) that mediates circulation related to sexual function. The conversion of L-arginine to NO is mediated by NOsynthase (NOS). Increasing local L-arginine levels increases NO and Cgmp. L-arginine restores endothelial-derived NO production in conditions associated with reduced NO production, i.e., in aging women, diabetes, hypercholesterolemia, and hypertension. Circulatory health improvement with Pycnogenol is understood to be associated with improved endothelial function and enhanced NO synthesis in diverse pathologies.

The first phase of sexual response in females is neurotransmitter-mediated, vascular smooth muscle relaxation, resulting in vaginal increase in flow, activation of mucosal glands, vaginal wall engorgement, vaginal luminal diameter expansion and increased clitoral perfusion.

Different types of microangiopathy, atherosclerosis, smoking, diabetes, and other cardiovascular diseases and drug treatments all interfere with these functions, reducing vaginal engorgement and mucosal activation and causing a reduction in clitoral perfusional and erectile alterations. NO is involved in all these responses. Also, in many post-menopausal women, vaginal atrophy, a decrease in sexual interest and function, may be NO-dependent. Estrogen level reduction or withdrawal may also play an important role in the regulation of vaginal NO functions (in nerves, smooth muscle, vascular endothelium and vaginal mucosa). The aim of this study was to evaluate the efficacy of Prelox Lady® administered for improving/controlling SD in healthy postmenopausal women with normal circulation.

Materials and Methods

The study included healthy, post-menopausal women in the age range of 45 to 55 years. In accordance with a recent protocol, the evaluation method used was the FSFI, a validated questionnaire (Table 16) with multidimensional scales for assessment of female sexual function. Normal women with SD were assessed with a defined screening program for healthy women previously screened for cardiovascular problems.

TABLE 16

Scoring for the FSFI

| Domain | Item Number | Score Range | Minimum Score Score | Maximum |
|---|---|---|---|---|
| Desire | 1, 2 | 1-5 | 2 | 10 |
| Arousal | 3, 4, 5, 6 | 0-5 | 0 | 20 |
| Lubrication | 7, 8, 9, 10 | 0-5 | 0 | 20 |
| Orgasm | 11, 12, 13 | 0-5 | 0 | 15 |

TABLE 16-continued

Scoring for the FSFI

| Domain | Item Number | Score Range | Minimum Score Score | Maximum |
|---|---|---|---|---|
| Satisfaction | 14, 15, 16 | 0 (or 1)-5* | 2 | 15 |
| Pain | 17, 14, 19 | 0-5 | 0 | 15 |

*Range for item 14 = 0-5; range for items 15 and 16 = 1-5

Table 16

Their main endocrinological functions (including thyroid functional values and other metabolic parameters) were within normal values. These women had not been included in previous studies. No clinically significant cardiovascular disease was present at the moment of inclusion. Their inclusion body-mass index (BMI) was <24. A satisfactory educational and cultural-social status was considered important for inclusion and for a full understanding and adherence to the study protocol. Sexual dysfunction and defined previous menopause, and full consent (after careful information about the study) were important inclusion criteria. The included women had no surgery or hormonal treatment within the past twelve months before inclusion or during the evaluation period. Prelox Lady® tablets contain a proprietary combination of 20 mg Pycnogenol®, 200 mg L-arginine, 200 mg L-citrulline and 50 mg rose hip extract. In this study the daily dosage was four tablets (two tablets/twice daily) for a total of eight weeks. The FSFI score was used to estimate the efficacy of Prelox Lady® on specific aspects and on the global sexual activity of women. Results were recorded at baseline, and after four and eight weeks of treatment.

A comparable group of women served as the control group and took similar tablets that did not include active substances in the same manner as the treatment group in single-blinded fashion. No medications or other supplements were used during the trial period, while daily vitamins and minerals were permitted.

Statistical Analysis

The aim of the registry was to analyze data from a group of 80 women, half of whom used active Prelox Lady® for at least eight weeks. The results were evaluated using analysis of variance (ANOVA with the Bonferroni correction) and the non-parametric Mann-Whitney U test.

It was concluded that at least 20 subjects completing the study/observation period in each group were necessary to obtain statistically meaningful information. This predefined number was chosen to overcome spontaneous or intra-individual variations and to overcome inter-individual variability in the FSFI score. As non-clinical condition SD in women may have peaking periods of important signs and symptoms followed by other periods of a lower level of signs and symptoms. Variations may be due to several unpredictable factors that include individual situations (i.e., stress levels), environmental and social factors, as well as habitual and occupational changes.

The FSFI Questionnaire: Factor Analysis and Scoring

In the original evaluation of the FSFI score system, a main component analysis (using varimax rotation) was performed to investigate the factor structure of the questionnaire. FSFI items had been selected on the basis of statistical criteria for item inclusion, among those high/moderate loading on one factor, low crossfactor loading, high/moderate test-retest reliability, and good discrimination between the FSAD and the control sample. In Rosen's original report, which was the basis of the present study, items were generally clustered in the predicted fashion and had relatively high factor loadings, supporting the global factoral validity of the final questionnaire. The items are balanced and could be used in different social settings. However, regional cultural variations and population factors may still have an unpredictable value.

Results:

TABLE 17 results of the FSFI questionnaire.

| | INCLUSION | 4 WEEKS | 8 WEEKS |
|---|---|---|---|
| 1. SEXUAL DESIRE OR INTEREST | | | |
| TREATMENT | 2.33; 1.2 | 3.6; 1.1 | 3.78; 1.4 |
| CONTROLS | 2.3; 1.1 | 2.2; 1 | 2.8; 1.1 |
| 2. LEVEL (DEGREE) OF SEXUAL DESIRE OR INTEREST | | | |
| T | 2.8; 1.1 | 3; 1.1 | 3.2; 1 |
| C | 2.9; 1.3 | 2.8; 1.4 | 2.9; 1 |
| 3. SEXUAL AROUSAL (HOW OFTEN) | | | |
| T | 2.21 | 2.9; 1 | 3.32 |
| C | 2.3; 1.2 | 2.2; 1.1 | 3.1; 1.2 |
| 4. LEVEL OF SEXUAL AROUSAL | | | |
| T | 2.1; 1.1 | 3.8; 1.2 | 4.1; 1.3 |
| C | 2.2; 1.2 | 2.2; 1 | 2.3; 1.2 |
| 5. CONFIDENCE (ABOUT AROUSAL) | | | |
| T | 2.23; 1.2 | 3.9; 1.1 | 3.8; 1 |
| C | 2.1; 1.2 | 2.2; 1.4 | 2.9; 1.2 |
| 6. HOW OFTEN SATISFIED WITH AROUSAL | | | |
| T | 2.71; 1.2 | 3.4; 1.2 | 3.3; 1.3 |
| C | 2.6; 1.3 | 2.7; 1 | 3.02; 1.1 |
| 7. HOW OFTEN BECOME LUBRICATED DURING S. ACTIVITY | | | |
| T | 3.1; 1.3 | 3.7; 1.2 | 4.2; 1.4 |
| C | 3; 1.1 | 3.1; 11 | 2.9; 1.1 |
| 8. HOW DIFFICULT TO BE LUBRICATED DURING S. ACTIVITY | | | |
| T | 3.9; 2.1 | 3.9; 1.3 | 4.1; 1.2 |
| C | 3.7; | 3.5; 1.1 | 3.2; 1.2 |
| 9. HOW OFTEN MAINTAIN LUBRICATION UNTIL END OF S. ACTIVITY | | | |
| T | 2.3; 1.3 | 4.4; 0.7 | 4.1; 1.3 |
| C | 2.1; 1.1 | 2.2; 1.1 | 2.3; 1 |
| 10. HOW DIFFICULT TO MAINTAIN LUBRICATION UNTIL END OF S. ACTIVITY | | | |
| T | 2.1; 1.1 | 4; 1.1 | 4.2; 1.1 |
| C | 2.1; 1 | 2.4; 1.2 | 2.3; 1.2 |

TABLE 17-continued results of the FSFI questionnaire.

|  | INCLUSION | 4 WEEKS | 8 WEEKS |
|---|---|---|---|
| 11. HOW OFTEN REACH ORGASM | | | |
| T | 2.1; 1 | 3.5; 1.1 | 3.4; 1.3 |
| C | 2.2; 1.2 | 2.3; 1.5 | 2.3; 1.2 |
| 12. HOW DIFFICULT REACH ORGASM | | | |
| T | 2.7; 1.2 | 4.3; 0.4 | 4.5; 1 |
| C | 2.5; 1.2 | 2.7; 1.5 | 2.7; 1.3 |
| 13. ABILITY TO REACH ORGASM | | | |
| T | 1.7; 1.9 | 3.5; 1.4 | 3.2; 1.2 |
| C | 1.65; 1.2 | 1.7; 1 | 1.6; 1.1 |
| 14. EMOTIONAL CLOSENESS | | | |
| T | 2.1; 1.6 | 4.2; 0.7 | 4.2; 1.1 |
| C | 2.1; 1.1 | 2.2; 1.1 | 2.2; 1.3 |
| 15. SATISFACTION ABOUT SEXUAL RELATIONSHIP | | | |
| T | 1.9; 1.1 | 3.8; 1.1 | 3.7; 1.3 |
| C | 1.7; 1.2 | 1.6; 1.2 | 1.4; 1.2 |
| 16. SATISFACTION WITH OVERALL SEXUAL LIFE | | | |
| T | 2.1; 1.2 | 3.3; 1.1 | 3.2; 1.1 |
| C | 2.2; 1.1 | 2.2; 1.4 | 2.4; 1.1 |
| 17. HOW OFTEN DISCOMFORT OR PAIN (AT PENETRATION) | | | |
| T | 2.1; 1.2 | 4.2; 0.4 | 4.1; 1.2 |
| C | 2.2; 1.1 | 2.3; 1.1 | 2.5; 1.1 |
| 18. HOW OFTEN DISCOMFORT OR PAIN (FOLLOWING PENETRATION) | | | |
| T | 2.1; 1.2 | 3.2; 0.9 | 3.1; 1.2 |
| C | 2.2; 1.1 | 2.3; 1.2 | 2.5; 1.1 |
| 19. LEVEL (DEGREE) OF DISCOMFORT/PAIN DURING/AFTER PENETRATION | | | |
| T | 2.1; 1.1 | 4.3; 0.4 | 4.2; 1.3 |
| C | 2; 1.2 | 2.2; 1 | 2.1; 1.2 |
|  | 44.64 | 70.9* | 71.71* |
|  | 44.15 | 45.0 ns | 47.4 |

Thirty-six out of 40 women in the Prelox Lady® group (aged 50.1±3.1 years; range 45-55 years) completed the study period of eight weeks. There were 39 comparable controls (aged 51.2±2.3 years; range 46-55 years) who completed the eight-week follow-up out of an initial 43 women. These dropouts resulted from non-medical reasons, due to failure to attend the check-ups or irregularities in completing the FSFI forms.

Results of the analysis of the 19-item questionnaire are shown in Table 17. The scores for the single items and standard deviations values are indicated: after four weeks there was a significant (P<0.05) improvement in the treatment group. The significant increase was sustained until the end of the eight-week observational period, Minor, insignificant changes were observed in the control group. The total median FSFI score in the Prelox Lady® treated group at inclusion was 44.6, which increased to 70.9 (P<0.05) after four weeks and remained at a comparable value after eight weeks (71.7; P<0.05 in comparison with the initial value).

In the control group the total FSFI score was 44.1 at inclusion (no significant difference to the treatment group), which marginally increased to 45.0 after four weeks and 47.4 after eight weeks. The changes were statistically insignificant. The total FSFI score increase in the treatment group was significantly higher after completion of the eight week observational period as compared to the control group (P=0.022). No side effects or intolerance problems were observed. Compliance was optimal as 97% of the active supplements and 97.3% of the non-active tablets were correctly used.

Discussion

The FSFI questionnaire has been developed as a multidimensional self-report instrument for assessing the key dimensions of sexual function in women. The questionnaire is considered psychometrically correct; it is simple to complete and has shown to be of value for clinical and nonclinical populations with SD. The questionnaire has been validated for the assessment of female sexual function and quality of life in several clinical trials or epidemiological studies. In postmenopausal women, alterations in vaginal perfusion and in the production of cervical and vaginal mucous may be an important factor in sexual dysfunction. This is more evident in diabetic women who often complain of vaginal dryness. In the treatment group of this study mucosal dryness improved, possibly leading to a facilitation of natural intercourse.

Mucous glycol-proteins (mucins) from human cervical/vaginal mucus include several macromolecules (i.e., serine, threonine, proline, sugars such as N-acetylglucosamine, N-acetylgalactosamine, galactose, sialic acid and fructose). This composition may be severely altered in postmenopausal and particularly in diabetic women. The response to stimulation with mucous production may be altered or delayed, which could result in a dryer mucosal surface. This may cause more difficulty during intercourse and also exposes women to subclinical infections. Microcirculation alterations in diabetic women have been described and quantified. It is possible that these important alterations, including an alteration in vasomotor responses, may have a strong association with sexual dysfunction in women. However, even in non-diabetic women the combined effects of mucosal aging and reduced hormonal levels may produce comparable lower level signs and symptoms.

Sexual dysfunction is a common problem for women, but it is seldom reported and discussed. Several physiological actions are involved, and there are very important psychological components.

Pharmaceutical treatments for female SD are not available at the moment. An attempt to treat SD with sildenafil in postmenopausal women was not effective. Also, hormonal treatment may cause important side effects. This study indicates a significant improvement in dryness, with resulting decrease in discomfort and pain can be obtained with Prelox Lady®. This in turn may relate to an increase in frequency of intercourse and a more satisfactory relationship. These observations are likely to be confirmed in larger studies with Prelox Lady® currently in progress with premenopausal and menopausal women.

A comparison of our study with the studies performed by Ito and co-workers shows better results in our study group. This may be due to a tighter defined age range, as the study of Ito et al. included women at ages ranging from 20 to more than 77 years.

Furthermore, Ito recruited women with different socio-cultural backgrounds. This study offers an interesting perspective in women's sexual function enhancement that calls for further clinical investigation.

The FSFI Questionnaire (Rosen's Female Sexual Function Index)

Sexual Desire or Interest is a Feeling that Includes Wanting to have a Sexual Experience, Feeling Receptive to a Partner's Sexual Initiation, and Thinking or Fantasizing about Having Sex.

1. How often did you feel sexual desire or interest?
Almost always or always
Most times (more than half the time)
Sometimes (about half the time)
A few times (less than half the time)
Almost never or never 2. How would you rate your level (degree) of sexual desire or interest?
Very high
High
Moderate
Low
Very low or none at all Sexual Arousal Includes Physical and Mental Aspects of Sexual Excitement. It May Include Feelings of Warmth or Tingling in the Genitals, Lubrication (Wetness), or Muscle Contractions.

3. How often did you feel sexually aroused ("turned on") during sexual activity or intercourse?
No sexual activity
Almost always or always
Most times (more than half the time)
Sometimes (about half the time)
A few times (less than half the time)
Almost never or never 4. How would you rate your level of sexual arousal ("turn on") during sexual activity or intercourse?
No sexual activity
Very high
High
Moderate
Low
Very low or none at all 5. How confident were you about becoming sexually aroused during sexual activity or intercourse?
No sexual activity
Very high confidence
High confidence
Moderate confidence
Low confidence
Very low or no confidence 6. How often have you been satisfied with your arousal (excitement) during sexual activity or intercourse?
No sexual activity
Almost always or always
Most times (more than half the time)
Sometimes (about half the time)
A few times (less than half the time)
Almost never or never 7. How often did you become lubricated ("wet") during sexual activity or intercourse?
No sexual activity
Almost always or always
Most times (more than half the time)
Sometimes (about half the time)
A few times (less than half the time)
Almost never or never 8. How difficult was it to become lubricated ("wet") during sexual activity or intercourse?
No sexual activity
Extremely difficult or impossible
Very difficult
Difficult
Slightly difficult
Not difficult 9. How often did you maintain your lubrication ("wetness") until completion of sexual activity or intercourse?
No sexual activity
Almost always or always
Most times (more than half the time)
Sometimes (about half the time)
A few times (less than half the time)
Almost never or never 10. How difficult was it to maintain your lubrication ("wetness") until completion of sexual activity or intercourse?
No sexual activity
Extremely difficult or impossible
Very difficult
Difficult
Slightly difficult
Not difficult 11. When you had sexual stimulation or intercourse, how often did you reach orgasm (climax)?
No sexual activity
Almost always or always
Most times (more than half the time)
Sometimes (about half the time)
A few times (less than half the time)
Almost never or never 12. When you had sexual stimulation or intercourse, how difficult was it for you to reach orgasm (climax)?
No sexual activity
Extremely difficult or impossible
Very difficult
Difficult
Slightly difficult
Not difficult 13. How satisfied were you with your ability to reach orgasm (climax) during sexual activity or intercourse?
No sexual activity
Very satisfied
Moderately satisfied
About equally satisfied and dissatisfied
Moderately dissatisfied
Very dissatisfied 14. How satisfied have you been with the amount of emotional closeness during sexual activity between you and your partner?
No sexual activity
Very satisfied
Moderately satisfied
About equally satisfied and dissatisfied
Moderately dissatisfied
Very dissatisfied 15. How satisfied have you been with your sexual relationship with your partner?
Very satisfied
Moderately satisfied
About equally satisfied and dissatisfied
Moderately dissatisfied
Very dissatisfied
16. How satisfied have you been with your overall sexual life?
Very satisfied
Moderately satisfied
About equally satisfied and dissatisfied
Moderately dissatisfied
Very dissatisfied
17. How often did you experience discomfort or pain during vaginal penetration?
Did not attempt intercourse
Almost always or always
Most times (more than half the time)
Sometimes (about half the time)
A few times (less than half the time)
Almost never or never
18. How often did you experience discomfort or pain following vaginal penetration?
Did not attempt intercourse
Almost always or always
Most times (more than half the time)
Sometimes (about half the time)
A few times (less than half the time)
Almost never or never
19. How would you rate your level (degree) of discomfort or pain during or following vaginal penetration?
Did not attempt intercourse
Very high
High
Moderate
Low
Very low or none at all Example 3

Synergistic Activities of Proanthocyanidin Extract-L-arginine/L-citrulline Combinations with Added *Rosa Canina* Extract for Female Sexual Function Women's sexual function is scored using the established "Female Sexual Function Index" (FSFI) questionnaire [Rosen et al., 2000]. The questionnaire allows to score prevalence of six subcategories (domains) related to female sexual function, with minimum and maximum scores given:

| | |
|---|---|
| Desire | 1.2-6 |
| Arousal | 0-6 |
| Lubrication | 0-6 |
| Satisfaction | 0.8-6 |
| Pain | 0-6 |

Adult women of all ages were investigated who presented with a score lower than four points out of maximum six points for all five domains.

The investigation depicts the number of responders to the intervention as detailed in the tables after four weeks treatment with a score equal to or higher than four points for all five domains.

Women responding with improvement as explained above to taking the following supply daily

| 20 mg Pycnogenol + 200 mg L-arginine + 200 mg citrulline | Rosa canina 50 mg |
|---|---|
| | Responders |
| 16/26 | 4/27 |
| 24/26 | |

| 20 mg Cocoa extract + 200 mg L-arginine + 200 mg citrulline | Rosa canina 50 mg |
|---|---|
| | Responders |
| 9/22 | 5/23 |
| 19/23 | |

| 20 mg Green tea extract + 200 mg L-arginine + 200 mg citrulline | Rosa canina 50 mg |
|---|---|
| | Responders |
| 11/24 | 4/24 |
| 20/23 | |

| 20 mg Grape seeds extract + 200 mg L-arginine + 200 mg citrulline | Rosa canina 50 mg |
|---|---|
| | Responders |
| 13/26 | 6/28 |
| 23/27 | |

| 20 mg cranberry extract + 200 mg L-arginine + 200 mg citrulline | Rosa canina 50 mg |
|---|---|
| | Responders/n |
| 13/26 | 4/25 |
| 21/25 | |

| 80 mg Grape seeds extract + 200 mg L-arginine + 200 mg citrulline | Rosa canina 50 mg |
|---|---|
| | Responders |
| 11/25 | 5/26 |
| 20/24 | |

The results show *Rosa canina* extract added to a mixture of 200 mg L-arginine+citrulline+a proanthocyanidin rich extract (Pycnogenol®, Cocoa, green tea, Grape seed, cranberry) plays a synergistic effect as measured by the number of women responding to the treatment by improvement of their sexual function. The obtained results on the FSFI evidence that the addition of *Rosa canina* or extracts thereof to a mixture consisting of a source of arginine and a source of proanthocyanidin are much better than the simple addition of the results obtained for *Rosa canina* alone on one hand and the results obtained for a mixture consisting of a source of arginine and a source of proanthocyanidin on the other hand (comparison with US 2004/137081 Rohdewald). This is the proof of an unexpected and surprising synergistic effect on female patients.

References

Rosen R, Brown C, Heiman J, Leiblum S, Meston C, Shabsigh R, Ferguson D, D'Agostino R Jr. The Female Sexual Function Index (FSFI): a multidimensional self-report instrument for the assessment of female sexual function. J Sex Marital Ther 26: 191-208, 2000.

Example 4

Synergistic Activities of Proanthocyanidin Extract-L-arginine Combinations with Added *Quercus robur* Extract for Male Sexual Function Men's sexual function is scored using the established "International Index of Erectile Function" (IIEF) questionnaire [Rosen et al., 1997]. A subset of only 6 questions (#1-5 plus 15) of the total 30 questions is related to erectile function with values ranging from minimum zero to 30.

To avoid communication of exact IIEF scores [0-30], men are judged as having moderate erectile problems at baseline with values 13-18 and after treatment achieving sufficient erectile abilities (values of 19 and above). Treatment duration was chosen as 2 weeks because after 4 weeks with Prelox® (US 2004/137081) the IIEF was previously published to reach 28/30. That does not leave room for further synergistic activities.

Erectile function total scores can be interpreted as follows:
Score Interpretation
0-6 Severe dysfunction
7-12 Moderate dysfunction
13-18 Mild to moderate dysfunction
19-24 Mild dysfunction
25-30 No dysfunction Men responding with Improvement as explained above

| 80 mg Pycnogenol + 2.8 g L-arginine | Quercus robur 100 mg |
|---|---|
| | Responders |
| 12/25 | 6/25 |
| 22/24 | |

| 80 mg Cocoa extract + 2.8 g L-arginine | Quercus robur 100 mg |
|---|---|
| | Responders |
| 10/23 | 4/20 |
| 17/21 | |

| 80 mg Green tea extract + 2.8 g L-arg | Quercus robur 100 mg |
|---|---|
| | Responders |
| 10/25 | 19/23 |
| 5/23 | |

| 80 mg Grape seeds extract + arg | Quercus robur 100 mg |
|---|---|
| | Responders |
| 8/19 | 4/20 |
| 15/20 | |

The results show that *Quercus robur* extract added to a mixture of 2.8 g L-arginine+a proanthocyanidin rich extract (Pycnogenol, Cocoa, green tea, Grape seed, cranberry) plays a synergistic effect as measured by the number of men responding to the treatment by improvement of their sexual function. The obtained results on the IIEF evidence that the addition of *Quercus robur* (oak wood) or extracts thereof to a mixture consisting of a source of arginine and a source of proanthocyanidin are much better than the simple addition of the results obtained for *Quercus robur* alone on one hand and the results obtained for a mixture consisting of a source of arginine and a source of proanthocyanidin on the other hand (comparison with US 2004/137081 Rohdewald). This is the proof of an unexpected and surprising synergistic effect on male patients.

Example 5

Synergistic Activities of Proanthocyanidin Extract-L-arginine Combinations with Added Combination of *Quercus robur* Extract and *Rosa canina* Extract for Male and Female Sexual Function Men responding with Improvement as explained above

| 80 mg Pycnogenol + 2.8 g L-arginine | Quercus robur 100 mg and Rosa canina 50 mg |
|---|---|
| | Responders |
| 13/26 | 7/26 |
| 23/25 | |

Women responding with Improvement as explained above

| 80 mg Pycnogenol + 2.8 g L-arginine | Quercus robur 100 mg and Rosa canina 50 mg |
|---|---|
| | Responders |
| 11/24 | 4/21 |
| 18/21 | |

The results show that the combination of *Quercus robur* extract and *Rosa canina* extract added to a mixture of 2.8 g L-arginine+a proanthocyanidin rich extract (Pycnogenol) play a synergistic effect as measured by the number of men and women responding to the treatment by improvement of their sexual function. The obtained results evidence that the addition of a mixture of *Quercus robur* (oak wood) or extracts thereof and *Rosa canina* or extracts thereof to a composition consisting of a combination of a source of arginine and a source of proanthocyanidin are much better than the simple addition of the results obtained for *Quercus robur* and *Rosa canina* on one hand and the results obtained for the composition consisting of a combination of a source of arginine and a source of proanthocyanidin on the other hand (comparison versus respectively US 2004/137081 and RU 2388811). This is the proof of an unexpected and surprising synergistic effect on male and female patients.

Example 6

Effects of L-arginine Added to a Combination of Proanthocyanidin Rich Extract and *Rosa Canina* Extract for Female Sexual Function Women responding with Improvement as explained above

| 80 mg Pycnogenol + Rosa canina 50 mg | 2.8 g L-arginine |
|---|---|
| | Responders |
| 13/27 | 5/26 |
| 24/26 | |

The results show that 2.8 g L-arginine added to a mixture of a proanthocyanidin rich extract (Pycnogenol) and *Rosa canina* extract plays a synergistic effect as measured by the number of women responding to the treatment by improvement of their sexual function. The obtained results evidence that the addition of a mixture of *Rosa canina* or extracts thereof and a source of proanthocyanidin to a source of arginine are much better than the simple addition of the results obtained for proanthocyanidin and *Rosa canina* on one hand and the results obtained for a source of arginine alone on the other hand (comparison versus WO 2008/115583 MINI JOHN). This is the proof of an unexpected and surprising synergistic effect on male and female patients.

The invention claimed is:

1. A method of treatment for improving sexual fitness or wellness or sexual enhancement of both sexes comprising:
   administering, to a subject in need of improved sexual fitness or wellness or sexual enhancement, an effective amount of a preparation including a combination of
      a first component, the first component being a source of proanthocyanidins containing rich extracts,
      a second component, the second component being a source of arginine,
      a third component, the third component being Rose hip and/or extracts thereof or *Quercus robur* and/or extracts thereof or a mixture thereof, and a suitable excipient,
   wherein said first, second and third components are present in the preparation, respectively, in a weight ratio of, 20-80:400-2800:50-150, and
   wherein said preparation is administered at a dosage of between 5 mg per day to 2000 mg per day.

2. The method of treatment according to claim 1, wherein the preparation consists in a combination of:
   a source of proanthocyanidins containing rich extracts,
   a source of arginine,
   Rose hip and/or extracts thereof and *Quercus robur* and/or extracts thereof, and a suitable excipient.

3. The method of treatment according to claim 1, wherein said source of arginine is arginine or citrulline or ornithine or any arginine precursors or derivatives thereof.

4. The method of treatment of claim 3, wherein said source of arginine is a salt or dipeptide of L-arginine and aspartic acid.

5. The method of treatment according to claim 1, wherein said source of proanthocyanidins containing rich extracts is originated from a plant extract or from a synthesized material.

6. The method of treatment of claim 5, wherein the plant extract is selected from the group consisting of proanthocyanidins containing extracts selected among extracts of pine bark, grape seed, apples, peanut skin, walnuts, pomegranates, raspberry, black currants, blueberry, almonds, tea, hawthorn, cocoa and combination thereof.

7. The method of treatment of claim 6, wherein the plant extract is originated from pine bark.

8. The method of treatment according to claim 1, wherein Rose hip and/or extracts thereof comprise carotenoids, tocopherols, tocotrienols, vitamin C, polyphenols and glycosides of mono- or di- or triacylglycerol compounds.

9. The method of treatment of claim 7, wherein the plant extract is originated from French maritime pine bark.

10. The method of treatment according to claim 1, wherein Rose hip and/or extracts thereof consist of *Rosa canina*.

11. The method of treatment according to claim 1, wherein the suitable excipient is a pharmaceutically acceptable excipient.

12. The method of treatment according to claim 1, wherein the preparation is in the form of a food preparation, a dietary supplement, a nutraceutical, or a beverage.

13. The method of treatment according to claim 1, wherein the preparation is a medicament.

14. A method of treatment for treating sexual dysfunction in both sexes comprising:
   administering, to a patient suffering from sexual dysfunction, an effective amount of a preparation including a combination of
      a first component, the first component being a source of proanthocyanidins containing rich extracts,
      a second component, the second component being a source of arginine,
      a third component, the third component being Rose hip and/or extracts thereof or *Quercus robur* and/or extracts thereof or a mixture thereof, and a suitable excipient,
   wherein said first, second and third components are present in the preparation, respectively, in a weight ratio of, 20-80:400-2800:50-150, and
   wherein said preparation is administered at a dosage of between 5 mg per day to 2000 mg per day.

* * * * *